United States Patent
Carter et al.

(10) Patent No.: US 10,398,494 B2
(45) Date of Patent: Sep. 3, 2019

(54) SURGICAL TOOLS FOR SPINAL FACET THERAPY TO ALLEVIATE PAIN AND RELATED METHODS

(71) Applicant: Medovex Corp., Cumming, GA (US)

(72) Inventors: Robert D. Carter, Apple Valley, MN (US); Adam L. Gullickson, Stillwater, MN (US); Scott M. W. Haufe, Niceville, FL (US); Seth Iverson, Carver, MN (US); Jacob Blank, Minneapolis, MN (US)

(73) Assignee: Medovex Corp., Cumming, GA (US)

( * ) Notice: Subject to any disclaimer, the term of this patent is extended or adjusted under 35 U.S.C. 154(b) by 591 days.

(21) Appl. No.: 15/093,148

(22) Filed: Apr. 7, 2016

(65) Prior Publication Data

US 2016/0213415 A1 Jul. 28, 2016

Related U.S. Application Data

(63) Continuation-in-part of application No. 14/810,683, filed on Jul. 28, 2015, now Pat. No. 9,980,771.

(Continued)

(51) Int. Cl.
*A61B 1/32* (2006.01)
*A61B 18/12* (2006.01)
(Continued)

(52) U.S. Cl.
CPC ...... *A61B 18/1206* (2013.01); *A61B 17/1671* (2013.01); *A61B 17/32002* (2013.01); *A61B 17/3417* (2013.01); *A61B 17/3421* (2013.01); *A61B 17/3494* (2013.01); *A61B 18/1233* (2013.01); *A61B 18/148* (2013.01); *A61B 18/1482* (2013.01); *A61B 18/1487* (2013.01); *A61B 17/848* (2013.01); *A61B 17/8897* (2013.01); *A61B 2017/0046* (2013.01); *A61B 2017/00119* (2013.01); *A61B 2017/00261* (2013.01); *A61B 2017/00353* (2013.01); (Continued)

(58) Field of Classification Search
CPC combination set(s) only.
See application file for complete search history.

(56) References Cited

U.S. PATENT DOCUMENTS 2,001,638 A * 5/1935 Tornsjo ................ A61B 17/34
                                                          600/561
2,012,362 A   8/1935 Vogel
(Continued)

FOREIGN PATENT DOCUMENTS

CN       2064221    10/1990
CN      102641152    8/2012
(Continued)

OTHER PUBLICATIONS

U.S. Appl. No. 29/553,207, filed Jan. 29, 2016, Carter et al.
(Continued)

*Primary Examiner* — Sameh R Boles
(74) *Attorney, Agent, or Firm* — Myers Bigel, P.A.

(57) ABSTRACT

Methods and surgical tools for treating back pain use a spinal facet debridement tool with cautery and denuding action and minimally invasive protocol that can denude and cauterize soft tissue associated with a synovial capsule of the spinal facet joint.

6 Claims, 26 Drawing Sheets

Related U.S. Application Data

(60) Provisional application No. 62/135,791, filed on Mar. 20, 2015, provisional application No. 62/043,537, filed on Aug. 29, 2014, provisional application No. 62/031,037, filed on Jul. 30, 2014, provisional application No. 62/288,638, filed on Jan. 29, 2016.

(51) Int. Cl.
*A61B 18/14* (2006.01)
*A61B 17/16* (2006.01)
*A61B 17/32* (2006.01)
*A61B 17/34* (2006.01)
*A61B 18/00* (2006.01)
*A61B 17/88* (2006.01)
*A61B 17/00* (2006.01)
*A61B 17/84* (2006.01)
*A61B 90/00* (2016.01)

(52) U.S. Cl.
CPC ........... *A61B 2017/00455* (2013.01); *A61B 2017/00929* (2013.01); *A61B 2017/3492* (2013.01); *A61B 2018/00005* (2013.01); *A61B 2018/0091* (2013.01); *A61B 2018/00208* (2013.01); *A61B 2018/00339* (2013.01); *A61B 2018/00595* (2013.01); *A61B 2018/00601* (2013.01); *A61B 2018/00642* (2013.01); *A61B 2018/00666* (2013.01); *A61B 2018/00702* (2013.01); *A61B 2018/00779* (2013.01); *A61B 2018/00988* (2013.01); *A61B 2018/1226* (2013.01); *A61B 2090/034* (2016.02); *A61B 2090/036* (2016.02); *A61B 2090/062* (2016.02); *A61B 2090/0803* (2016.02); *A61B 2090/0811* (2016.02); *A61B 2090/0814* (2016.02); *A61B 2217/005* (2013.01); *A61B 2217/007* (2013.01); *A61B 2218/002* (2013.01); *A61B 2218/007* (2013.01)

(56) References Cited

U.S. PATENT DOCUMENTS

| | | |
|---|---|---|
| 4,002,169 A | 1/1977 | Cupler, II |
| 4,314,568 A | 2/1982 | Loving |
| 4,658,819 A | 4/1987 | Harris et al. |
| 4,813,939 A | 3/1989 | Marcus |
| 4,969,885 A | 11/1990 | Farin |
| 4,983,179 A | 1/1991 | Sjostrom |
| 4,991,578 A | 2/1991 | Cohen |
| 5,312,332 A | 5/1994 | Bales et al. |
| 5,364,395 A | 11/1994 | West, Jr. |
| 5,545,195 A | 8/1996 | Lennox et al. |
| 5,569,290 A | 10/1996 | McAfee |
| 5,573,533 A | 11/1996 | Strul |
| 5,584,843 A | 12/1996 | Wulfman et al. |
| 5,618,296 A | 4/1997 | Sorensen et al. |
| 5,633,578 A | 5/1997 | Eggers et al. |
| 5,693,045 A | 12/1997 | Eggers |
| 5,807,395 A | 9/1998 | Mulier et al. |
| 5,819,734 A | 10/1998 | Deily et al. |
| 5,849,023 A | 12/1998 | Mericle |
| 5,855,576 A | 1/1999 | LeVeen et al. |
| 5,865,810 A | 2/1999 | Perry et al. |
| 5,904,681 A | 5/1999 | West, Jr. |
| 5,941,876 A | 8/1999 | Nardella et al. |
| 5,957,863 A | 9/1999 | Koblish et al. |
| 6,007,533 A | 12/1999 | Casscells et al. |
| 6,032,673 A | 3/2000 | Savage et al. |
| 6,142,992 A | 11/2000 | Cheng et al. |
| 6,214,001 B1 | 4/2001 | Casscells et al. |
| 6,406,424 B1 | 6/2002 | Williamson, IV et al. |
| 6,416,490 B1 | 7/2002 | Ellis et al. |
| 6,454,764 B1 | 9/2002 | Fleenor et al. |
| 6,524,238 B2 | 2/2003 | Velikaris et al. |
| 6,579,281 B2 | 6/2003 | Palmer et al. |
| 6,610,059 B1 | 8/2003 | West, Jr. |
| 6,663,628 B2 | 12/2003 | Peters |
| 6,770,070 B1 | 8/2004 | Balbierz |
| 6,827,725 B2 | 12/2004 | Batchelor et al. |
| 6,979,332 B2 | 12/2005 | Adams |
| 7,001,333 B2 | 2/2006 | Hamel et al. |
| 7,052,494 B2 | 5/2006 | Goble et al. |
| 7,150,747 B1 | 12/2006 | McDonald et al. |
| 7,326,177 B2 | 2/2008 | Williamson, IV et al. |
| 7,331,956 B2 | 2/2008 | Hovda et al. |
| 7,361,174 B2 | 4/2008 | Bee et al. |
| 7,674,263 B2 | 3/2010 | Ryan |
| 7,736,361 B2 | 6/2010 | Palanker et al. |
| 7,789,879 B2 | 9/2010 | Palanker et al. |
| 7,942,874 B2 | 5/2011 | Eder et al. |
| 8,012,153 B2 | 9/2011 | Woloszko et al. |
| 8,043,286 B2 | 10/2011 | Palanker et al. |
| 8,167,879 B2 | 5/2012 | Haufe |
| 8,323,276 B2 | 12/2012 | Palanker et al. |
| 8,343,189 B2 | 1/2013 | Assell et al. |
| 8,394,129 B2 | 3/2013 | Lopez et al. |
| 8,500,727 B2 | 8/2013 | Aramayo |
| 2001/0000531 A1 | 4/2001 | Casscells et al. |
| 2002/0165549 A1 | 11/2002 | Owusu-Akyaw et al. |
| 2003/0153926 A1 | 8/2003 | Schmieding et al. |
| 2003/0195392 A1 | 10/2003 | Hamel et al. |
| 2004/0030330 A1 | 2/2004 | Brassell et al. |
| 2004/0078037 A1 | 4/2004 | Batchelor et al. |
| 2005/0245923 A1 | 11/2005 | Christopherson et al. |
| 2006/0058780 A1 | 3/2006 | Edwards et al. |
| 2006/0064101 A1 | 3/2006 | Arramon |
| 2006/0094976 A1 | 5/2006 | Bleich |
| 2006/0095059 A1 | 5/2006 | Bleich et al. |
| 2006/0100501 A1 | 5/2006 | Berkelman et al. |
| 2006/0178670 A1 | 8/2006 | Woloszko et al. |
| 2007/0049920 A1 | 3/2007 | McClurken et al. |
| 2007/0129719 A1 | 6/2007 | Kendale et al. |
| 2007/0293724 A1 | 12/2007 | Saadate et al. |
| 2008/0015565 A1 | 1/2008 | Davison |
| 2008/0161670 A1 | 7/2008 | King et al. |
| 2008/0163870 A1 | 7/2008 | Kusunoki et al. |
| 2008/0188848 A1 | 8/2008 | Deutmeyer et al. |
| 2008/0249553 A1 | 10/2008 | Gruber et al. |
| 2009/0012362 A1 | 1/2009 | Kucklick |
| 2009/0093683 A1 | 4/2009 | Richard et al. |
| 2010/0010449 A1 | 1/2010 | Leibowitz et al. |
| 2010/0145142 A1 | 6/2010 | Begemann et al. |
| 2011/0087217 A1 | 4/2011 | Yates et al. |
| 2012/0179070 A1 | 7/2012 | Pommer et al. |
| 2013/0190809 A1 | 7/2013 | Vidlund et al. |
| 2013/0289399 A1 | 10/2013 | Choi et al. |
| 2014/0046380 A1 | 2/2014 | Asfora |
| 2014/0100567 A1 | 4/2014 | Edwards |
| 2014/0324044 A1 | 10/2014 | Haufe et al. |
| 2016/0030106 A1 | 2/2016 | Carter et al. |

FOREIGN PATENT DOCUMENTS

| | | |
|---|---|---|
| CN | 202637105 | 1/2013 |
| WO | WO 97/33523 A1 | 9/1997 |
| WO | WO 2005/058132 A2 | 6/2005 |
| WO | WO 2008/060277 A2 | 5/2008 |
| WO | WO 2014/176141 A2 | 10/2014 |

OTHER PUBLICATIONS

International Search Report and Written Opinion for related PCT Application No. PCT/US2015/040867, dated Jan. 4, 2016, 24 pages.
International Search Report and Written Opinion for PCT Application No. PCT/US2014/034743, dated Dec. 15, 2015, 21 pages.

* cited by examiner

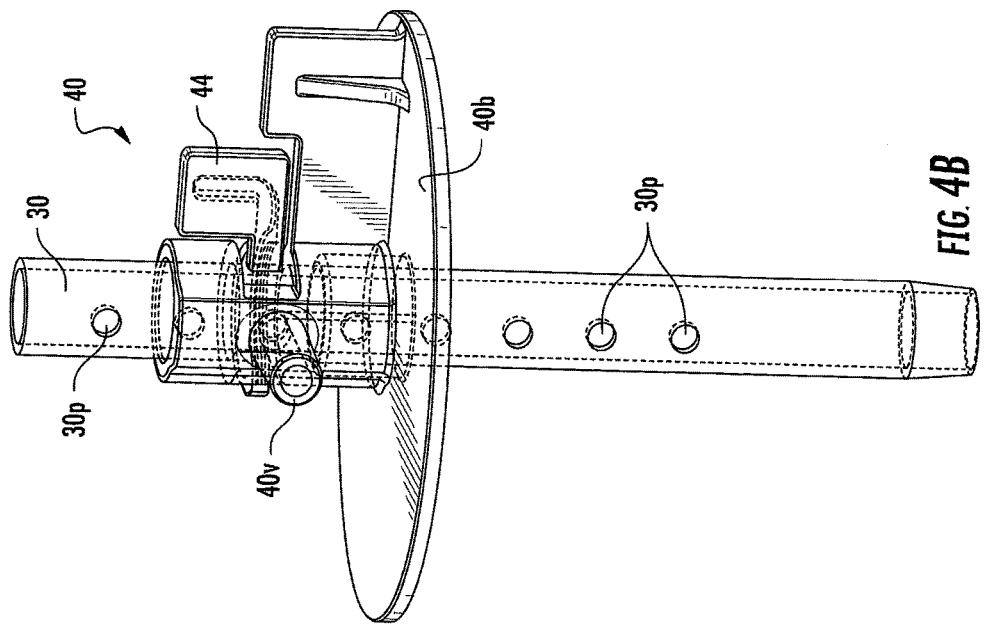
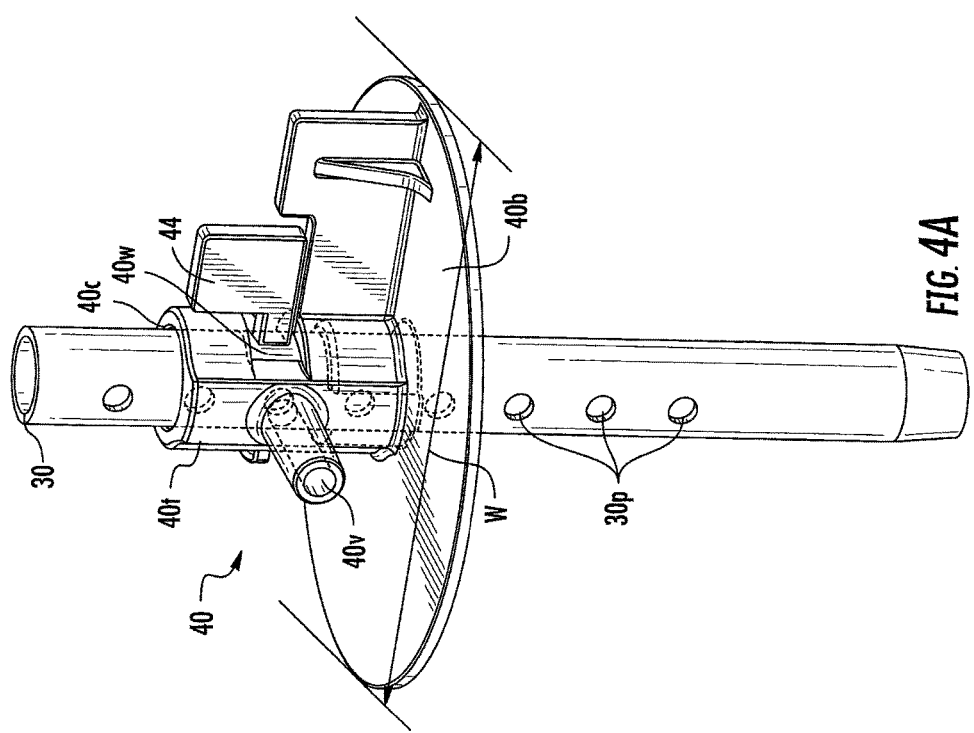

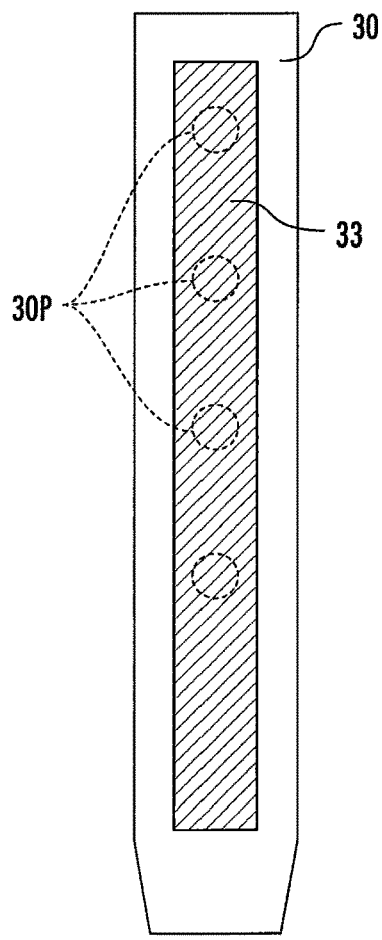
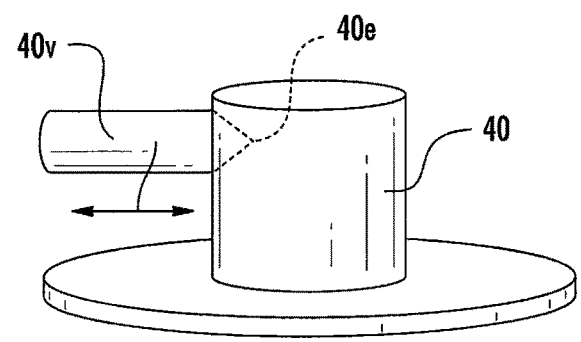
FIG. 5B
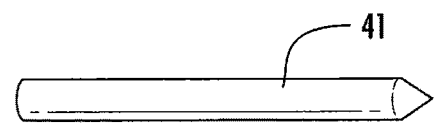
FIG. 5C
FIG. 5A
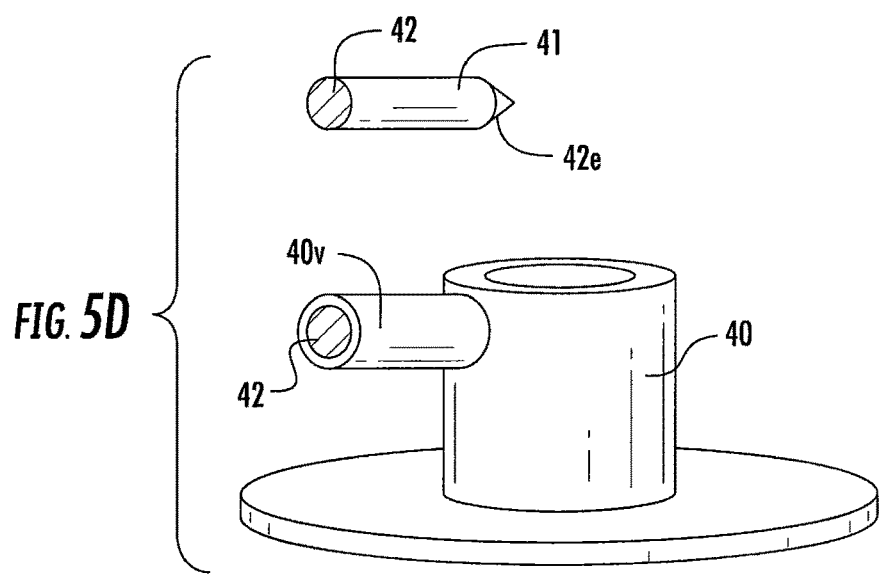
FIG. 5D

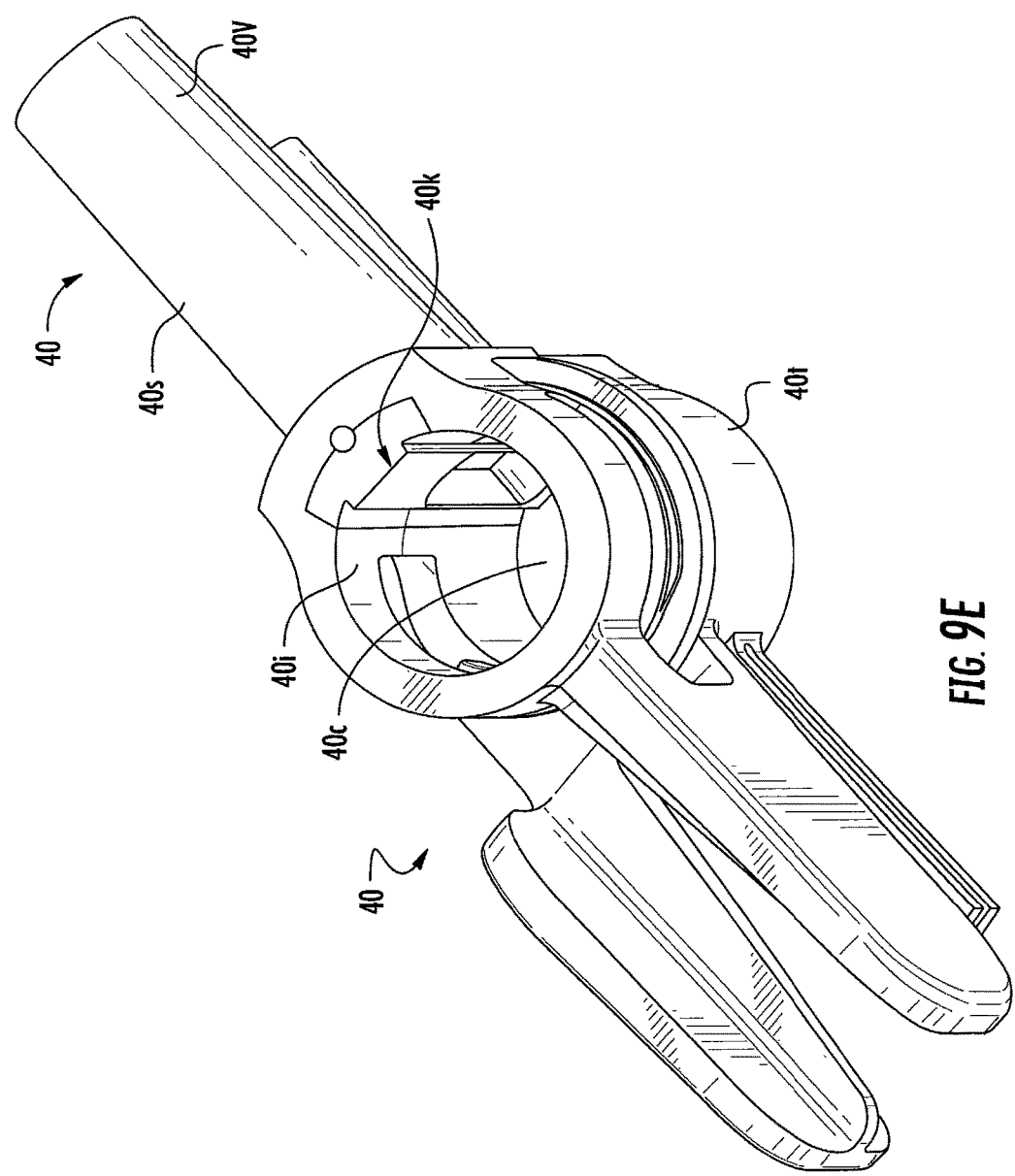

SURGICAL TOOLS FOR SPINAL FACET THERAPY TO ALLEVIATE PAIN AND RELATED METHODS

RELATED APPLICATIONS

This application claims the benefit of and priority to U.S. Provisional Patent Application Ser. No. 62/288,638 filed Jan. 29, 2016. This application is also a continuation-in-part of U.S. patent application Ser. No. 14/810,683, filed Jul. 28, 2015, which claims the benefit of and priority to U.S. Provisional Patent Application Ser. No. 62/031,037 filed Jul. 30, 2014, U.S. Provisional Patent Application Ser. No. 62/043,537 filed Aug. 29, 2014, and U.S. Provisional Patent Application Ser. No. 62/135,791 filed Mar. 20, 2015, the contents of which are hereby incorporated by reference as if recited in full herein.

FIELD OF THE INVENTION

The present invention relates to spinal medical procedures.

BACKGROUND

The facet joint is unique in that it has innervations via a single nerve source. For many years, a process of facet joint rhizotomy (RFL) has been utilized to provide temporary relief of spinal arthritis pain. RFL procedures involve cryotherapy or radiofrequency techniques to either freeze or burn the nerve. RFL is temporary because the nerve is destroyed at a point between the dorsal root ganglion (the nerve cell's body) and the end plate receptors (pain stimulation points on the joint) and thus, like any peripheral nerve, the nerve gradually regenerates and the pain eventually returns. Most RFL procedures last between 4 and 8 months and must be repeated when the pain returns for the rest of the patient's life for effective pain relief. Another option involves spinal fusion which is an expensive and relatively complex surgery with a success rate of only around 50% for spinal arthritis and few spine surgeons would perform such a surgery for spinal arthritis. Spinal fusion involves inserting rods and screws into the spine to permanently lock the joints.

Alternatively, upon proper training, a facet treatment (which can be described as a debridement procedure) can be performed on a cervical, thoracic or lumbar facet joint of a human spine. During facet debridement, the synovial capsule between facets is removed so as to denude the bone and denervate the joint (preventing reinnervation).

In the past, it is believed that only a few surgeons have been able to carry out a facet debridement procedure. The procedure was carried out using a plurality of separate instruments including a long wire hand burr to denude tissue and a cauterization tool to cauterize remaining tissue. Cauterization may be needed to stop bleeding, to prevent regrowth of removed tissue, and/or for other purposes. This often means that a surgeon must revisualize the operative site after changing instruments and locate the area to be cauterized. This can be especially problematic in laparoscopic procedures. Specifically, the surgeon must remove the grinder or other mechanical cutting instrument from a cannula, insert a cauterization instrument, and then cauterize the appropriate region.

SUMMARY OF EMBODIMENTS OF THE INVENTION

Embodiments of the present invention provide relatively rapid, minimally invasive and cost effective treatments for long term, typically permanent, pain relief for spinal arthritis pain.

Some embodiments are directed to methods of minimally invasively treating a patient for back pain, including, for example spinal facet arthritis.

The method can be carried out as an outpatient procedure.

Embodiments of the invention provide surgical systems with a guide cannula having at least one exhaust port and a hand grip member that is attached to the guide cannula (integrally or releasably attached) to allow for a twist and push action of the guide cannula.

The target spinal facet joint can be a lumbar spinal facet joint and the cannula and debrider tool can extend out of the patient at an angle of between about 10-40 degrees laterally, perpendicular to the target spinal facet joint.

The target spinal facet joint can be a cervical or thoracic spinal facet joint and the cannula and debrider tool can extend out of the patient at an angle of between about 0-10 degrees laterally, perpendicular to the target spinal facet joint.

Systems for the therapy can include an electrocautery generator that operates with a power curve having a maximum wattage of 50 Watts, typically about 40 Watts.

Embodiments of the invention are directed to methods of minimally invasively treating a patient for back pain. The methods include: (a) introducing a guide cannula into the patient so that a distal end resides proximate a target spinal facet joint; (b) attaching the guide cannula to an external tubular support member before, during or after the introducing step; then (c) denuding and cauterizing soft tissue at the target spinal facet joint, serially or concurrently, using a tool with a denuding and cauterization head that extends through the guide cannula. The denuding is carried out by rotating the head of the tool to remove an end plate receptor region comprising the synovial capsule of the spinal facet joint thereby treating back pain. The method also includes (d) suctioning fluid (heated air/gas) from the guide cannula and out of a vacuum port in the tubular support member during the cauterizing to exhaust heat generated from the cauterizing.

The guide cannula can have a plurality of longitudinally spaced apart heat exhaust ports, on a keyed or keyless surface.

The attaching can be carried out to lockingly engage an external portion of the guide cannula at a desired user adjustable height to position a distal end of the guide cannula at the target spinal facet joint before the denuding and cauterizing is carried out.

The introducing step can be carried out by concurrently manually rotating and pushing the guide cannula inward toward the target spinal facet joint over a dilation tube to position the distal end of the guide cannula proximate the target spinal facet joint before the denuding and cauterizing.

The method can include concurrently rotating and pushing the guide cannula inward toward the target spinal facet joint before attaching the guide cannula to the external stabilizer.

The concurrent rotating and pushing can be carried out using a hand grip attached to an external portion of the guide cannula.

The introducing step can be carried out by first inserting a k-wire or pin into the patient into bone at the target spinal facet joint, then inserting a dilation tube over the k-wire or pin into the patient, then inserting the guide cannula over the dilation tube. A hand grip can be attached to the guide cannula before, during or after the guide cannula is inserted over the dilation tube so that the dilation tube and k-wire or pin extend out of the hand grip above the guide cannula. Then a user can concurrently rotating and pushing inward against the hand grip to cut through tissue adjacent the target spinal facet joint and thereby position a distal end of the guide cannula at the target spinal facet joint.

The introducing step can visually confirm the guide cannula is in a desired location by referring to visual guide marks on the k-wire or pin above the hand grip.

The method can include, before the cauterizing and denuding, connecting the tool to an electrosurgical generator with an RF source. The cauterizing can be carried out using a power curve with a maximum output wattage of 50 Watts, a maximum current of 1000 mA, and a maximum voltage in a range of 180V and 220 V.

The power curve for the electrosurgical generator can have a maximum output wattage of 40 Watts, a maximum current of 1000 mA, and a maximum voltage in a range of 180 V and 220 V (optionally with an ohmic range of 0-3000 ohms).

Yet other embodiments are directed to surgical tools for spinal facet surgical procedures for alleviating spinal pain. The surgical tools include a guide cannula with a wall surrounding a cylindrical channel, the wall having a plurality of longitudinally spaced apart fluid ports extending therethrough. The surgical tools also include an external tubular support member with a base configured to rest against skin of a patient. The base holds a tube of the tubular support member that extends outward above the base and comprises at least one vacuum port. The tube of the tubular support member comprises a fluid chamber in fluid communication with the vacuum port that extends about an outer wall of the guide cannula. The fluid chamber has an inner wall with upper and lower ends that reside adjacent the outer wall of the guide cannula. The inner wall travels laterally outward a distance as it moves longitudinally away from each of the upper and lower ends to define an increased volumetric segment extending about the perimeter of the outerwall of the guide cannula. When assembled, the at least one vacuum port is in fluid communication with at least one of the guide cannula fluid ports.

The tube that extends outward from the base can hold an arm that extends perpendicularly outward from an axial direction of the tube about the vacuum port. The arm can releasably attach to a conduit which engages a vacuum source.

The guide cannula fluid ports can be heat exhaust ports and/or can remain closed until selectively opened by a user.

The plurality of longitudinally spaced apart fluid ports can be between 3-10.

The longitudinally spaced apart fluid ports can be in-line.

The arm of the tube held by the base that connects to a vacuum source can have a length that is between 1 and 3 inches.

The surgical tools can include a hand grip member configured to attach to the guide cannula to thereby allow a user to concurrently rotate and push against the guide cannula.

The hand grip member can have an open center channel extending therethrough with a circumferentially extending stop surface that releasably engages a proximal end of the guide cannula.

The hand grip member can include a longitudinally extending recess that slidably engages a longitudinally extending protrusion on the guide cannula. The longitudinally extending guide protrusion can hold the longitudinally spaced apart fluid ports.

The surgical tools can include a k-wire or guide pin that has visual markings thereon for allowing a user to determine a depth of a distal end of the guide cannula relative to the k-wire or guide pin when the k-wire or guide pin is in bone at a target spinal facet joint.

Yet other embodiments are directed to surgical tools that include an external stabilizer configured with a bottom surface that resides against skin of a patient. The stabilizer has an upwardly extending tube with a through channel that is held by the base and the tube has a wall that includes a vacuum port extending therethrough. The tube that extends upwardly from the base can hold an arm that extends perpendicularly outward from an axial direction of the tube about the vacuum port. The arm is adapted to attach to a vacuum source.

The surgical tool can be used in combination with a guide cannula. The guide cannula can have a cylindrical wall that surrounds an open through-channel. The wall can include a plurality of longitudinally spaced apart ports extending though the wall. The stabilizer can be sized and configured to releasably hold the guide cannula while allowing the guide cannula to align at least one of the guide cannula ports with the stabilizer tube vacuum port. The bottom surface of the stabilizer can have a perimeter with a width that is between about 2-6 inches.

The surgical tool can be used in combination with a hand grip that detachably engages the guide cannula. The hand grip can have an open center channel that is concentric with the guide cannula channel.

Yet other embodiments are directed to spinal facet therapy systems. The systems include an electrosurgical generator having a defined operational power curve with a maximum wattage of 60 Watts and a spinal facet therapy tool with an elongate rotatable shaft. The shaft has a distal end with a cautery element. The tool is in communication with the electrosurgical generator and is configured to automatically rotate at between about 10 rpm to about 5000 rpm to remove an end plate receptor region with the synovial capsule of the spinal facet joint. The electrosurgical generator supplies power to the cautery element while the shaft rotates or is stationary. The system also includes a guide cannula with at least one fluid port extending through a longitudinally extending wall thereof, the guide cannula configured to hold the tool shaft during an active treatment. The system also includes a stabilizer residing against skin of a patient and holding the guide cannula therein during the active treatment. The stabilizer includes at least one vacuum port in fluid communication with the guide cannula at least one fluid port and a vacuum source to thereby suction heat from the guide cannula when the cautery element is cauterizing.

The tool can have an onboard electrical motor. The electrosurgical generator can include a Field-Programmable Gate Array (FPGA) architecture for controlling output based on the defined power curve.

The electrosurgical generator can be held in a housing that also holds a power source for the motor.

The power curve can have a maximum output wattage of 50 Watts, a maximum current of 1000 mA, and a maximum voltage in a range of 180V-220 V.

The power curve can have a maximum output wattage of 40 Watts, a maximum current of 1000 mA, and a maximum voltage of 180V-220 V (optionally with an ohmic range some or all of 0-3000 ohms).

The spinal therapy system can include a hand grip member that can be configured to detachably couple to the guide cannula to thereby allow a user to concurrently rotate and push against the guide cannula to place the guide cannula in a desired position prior to inserting the tool shaft into the guide cannula.

The hand grip member can have an open center channel extending therethrough with a circumferentially extending stop surface that releasably engages a proximal end of the guide cannula.

The hand grip member can include a longitudinally extending recess that slidably engages a longitudinally extending protrusion on the guide cannula. The longitudinally extending guide cannula protrusion can hold the longitudinally spaced apart fluid ports.

The spinal therapy system can include a k-wire or guide pin that has visual markings thereon for allowing a user to determine a depth of a distal end of the guide cannula relative to the k-wire or guide pin when the k-wire or guide pin is in bone at a target spinal facet joint.

The cautery element can be or comprise a linear cautery element that extends straight across a distal face of the distal end of the shaft. The distal end of the shaft can also includes first and second diametrically opposing tissue scraping members that face each other across the linear cautery element.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 4A is an enlarged side perspective views of an exemplary external tubular member holding an exemplary guide tube, shown with the tubular member with a transparent body/wireframe to illustrate the underlying guide tube according to embodiments of the present invention.

FIG. 4B is a front view of the device shown in FIG. 4A.

FIG. 5A is a schematic illustration of a guide tube with a cover over the vacuum ports according to embodiments of the present invention.

FIGS. 5B-5D schematically illustrates optional piercing elements that may be provided to open closed guide cannula fluid ports according to embodiments of the present invention.

FIG. 9E is an enlarged, top perspective view of a tubular support member that can cooperate with a guide cannula according to embodiments of the present invention.

DETAILED DESCRIPTION OF EMBODIMENTS OF THE INVENTION

Figure 1:
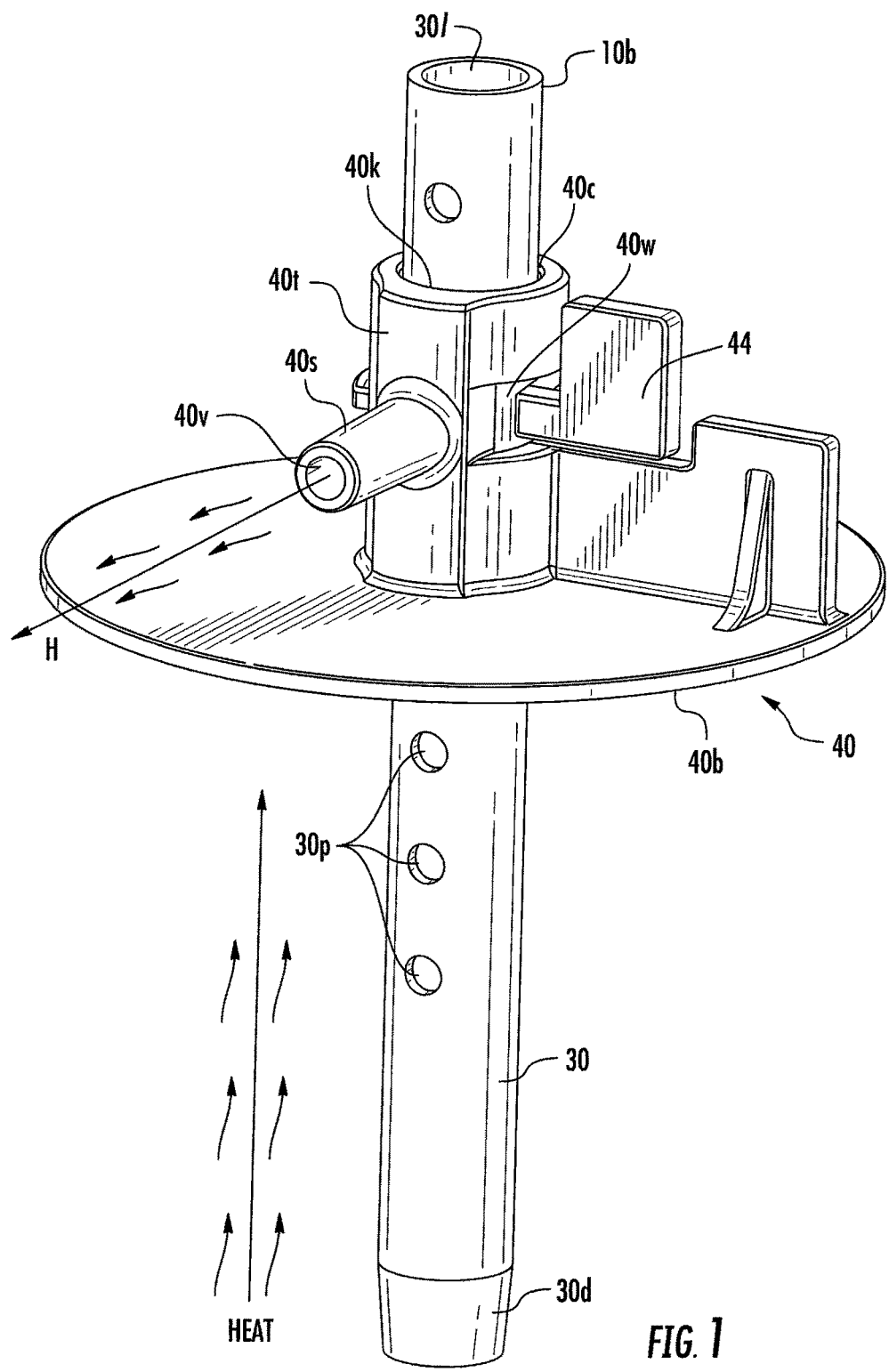
FIG. 1 is a side view of a guide cannula held by a cooperating member according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. The abbreviations "FIG." and "Fig." are used interchangeably with the word "Figure" in the specification and drawings. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise. In the claims, the word "a" with respect to an element is intended to include one or more of such elements and is not limited to a single such element unless stated otherwise.

The term "about" means that the recited number or value can vary by +/−20%.

The term "sterile" means that the noted device or material meets or exceeds defined medical guidelines of cleanliness as is well known to those of skill in the art to be substantially (if not totally) without contaminants so as to be suitable for medical uses and/or comply with defined medical guidelines, rules and/or regulations.

Embodiments of the invention are suitable for human or animal use, and are particularly suitable for human use.

The term "fluted" and derivatives thereof refer to recesses, typically flat or concave grooves, on one or more of the inner wall, outer wall, or shaft of a barrel, drive shaft, rotatable head or column of a surgical tool.

The term "denudement" and derivatives thereof refer to a procedure to polish, (gently) grind, scrape, file, grate, cleanse and/or rasp away soft tissue of facet joints to thereby denude tissue and uncover or expose the underlying bone without cutting into or removing the bone (e.g., in contrast to a sharp cutting edge like a knife). The denudement tool can have a surface that has an abrasive texture and/or configuration which may include small teeth.

The term "debridement" and derivatives thereof refer to the removal of soft tissue associated with an end plate receptor region of a target spinal facet joint including the synovial capsule and tissue scraping of an outer boney surface of the joint.

Generally stated, embodiments of the invention allow spinal facet joint debridement to remove the end plate receptor region which includes the synovial capsule and outer surface of the joint. Once the synovial capsule and outer surface of the joint are denuded, the nerves have nowhere to re-adhere to the joint and thus the joint is permanently denervated (communication between the facet joint and the brain is gone). In studies carried out by one of the inventors, pain relief is permanent in 75-80% of patients. While the joint continues to have arthritis, the patient's perception of the pain is gone as pain is what the brain perceives it to be and the patient simply does not feel the spinal pain. The joints have no worse decay then they would with the currently utilized RFL procedure since both utilize a denervation technique where the pain signals are severed between the brain and the joint.

Advantageously, while the current RFL procedure is a temporary treatment of pain, the spinal facet debridement procedure is a permanent alleviation of pain at the treated spinal facet joint. Thus, the spinal facet debridement procedure is cost effective. For example, currently, people who undergo RFL procedures may have them performed around twice a year for the duration of their lives, while the spinal facet debridement procedure is done once for the affected area. As people age, they may need other areas of the spine treated; for example, a person who has a low back debrided may eventually need the neck debrided. This is similar to the current RFL, in which only a small segment of the spine is done at one time for both patient comfort and time constraints. Usually two or three levels, bilaterally, are performed for either procedure.

Referring now to the figures, FIG. 1 illustrates a guide cannula 30 (also interchangeably termed a "guide tube" and a "working portal") and a tubular support member 40 that snugly holds the guide cannula 30 while allowing a user to adjust a height of the tube below the tubular support member 40. That is, the tubular support member 40 can include a height adjustment member 44 that cooperates with the guide tube 30 so as to allow a user to adjust where the tubular support member 40 holds the tube 30 thereby adjusting the height of the device 30 inside a patient body and/or below the bottom of the base 40b.

Figure 2:
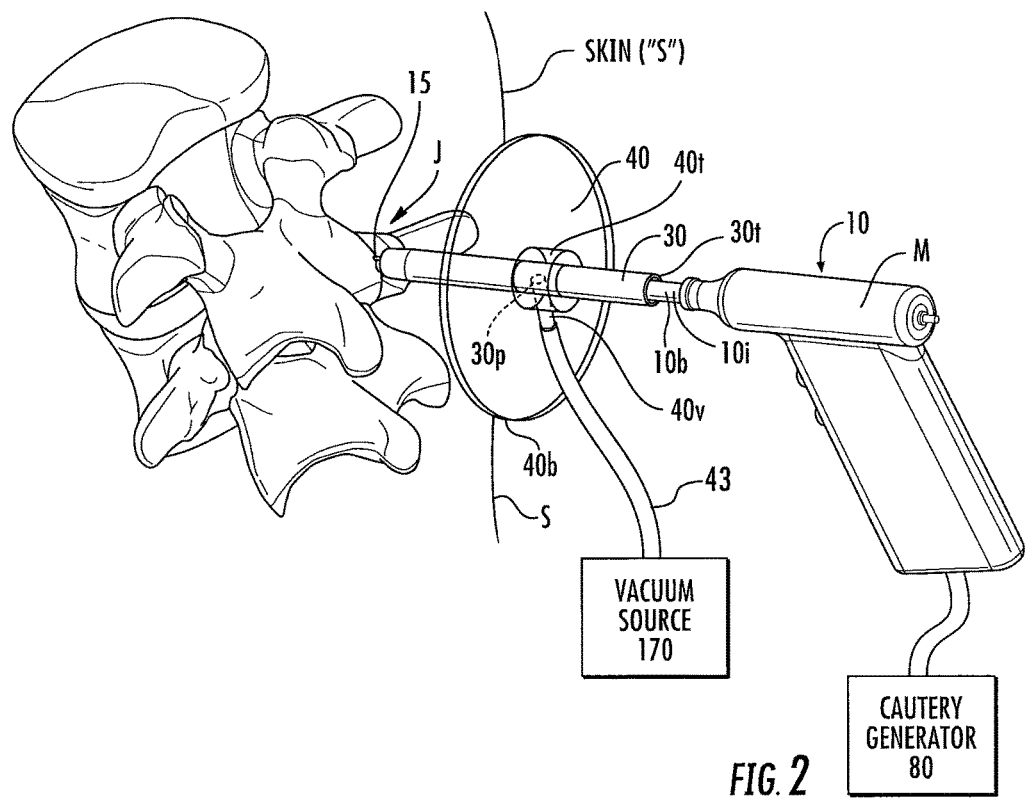
FIG. 2 is a schematic illustration of a guide cannula and cooperating member in line with a target spinal facet joint, with a combination tissue removal (denudement) and cauterization tool inserted according to embodiments of the present invention.

The tubular support member 40 includes a tubular body 40t with a lower surface or base 40b that has a larger cross-sectional or surface area than the tubular body 40t and can reside against skin S of a patient (FIG. 2). The barrel 10b of the surgical tool 10 (FIG. 2, 7A, 7C) can extend through a lumen 30l of the guide cannula 30 while the guide cannula 30 is held in a desired height position by the tubular support member 40.

The tool head 15 can have a aperture that merges into a pin receiving channel 11 (FIG. 12) for guiding placement over a pin or guidewire, for example.

In the embodiment shown in FIGS. 1 and 4A-4D, the height adjustment member 44 can be biased to have a "normal" position whereby it snugly resides against an outer surface of the guide tube 30 and can extend inward inside a window 40w in the tube 40t. A user can pull, pinch, press, depress or otherwise release or loosen the lateral position of the adjustment member 44 away from the outer surface of the guide cannula 30 thereby allowing the guide cannula 30 to be slid up or down inside the tube 40t.

The tubular support member 40 can optionally cooperate with or include a base 40b that provides some stabilization of the guide cannula to form an external stabilizer. The base 40b can be integral to the tubular support member or releasably attached thereto as shown, for example, in FIGS. 15A and 18A. Where used for stabilization, the base 40b may have a structure that provides the stabilization during the therapy with the dilation tube removed and the shaft 10b therein or other cooperating members (i.e., guidewires) may be used therewith. In some embodiments, a clinician can manually press against the tubular member 40 with one hand to force the base 40b against the skin of the patient and provide a suitable retention force to keep the tubular member 40 and guide cannula 30 in a desired position about a target spinal facet joint.

FIGS. 1, 2 and 4A-4D also show that the tubular support member 40 can include at least one vacuum port 40v (shown as a single vacuum port, but more than one may be optionally used). The vacuum port 40v can be configured as a flexible, rigid or semi-rigid tube segment 40s that extends (typically radially) outward from the tube 40t that holds the guide cannula 30. The guide cannula 30 can include at least one fluid port 30p that is in fluid communication with the vacuum port 40v during operation of the surgical tool 10. The vacuum port 40v can connect to a vacuum source 170 that can suction fluid (typically only heated air) from a therapy site to inside the guide cannula 30, out a selected port 30p and optionally into the vacuum port 40v and/or up out an upper end of the guide cannula (FIG. 18B).

With reference to FIG. 2, the spinal facet therapy delivery tool (e.g., "debrider" tool) 10 has a head 15 that contacts target tissue and the tool barrel 10b and/or head 15 is rotatable for denudement of the target tissue. The tool 10 can connect to a cautery generator 80. The cautery generator 80 is also known as an "electrosurgical generator" and "RF power generator." The vacuum port 40v can connect to a vacuum or suction source 170 via tubing 43.

The cautery generator 80 can be any appropriate power, electro-surgery generator including third party generators and/or a custom generator that is dedicated for use in spinal facet surgery, e.g., configured for use only with the tools 10. If third party generators are used, the tool 10 can include a control circuit C that can communicate with a selected generator input so as to be able to operate with multiple different generators. For example, a computer look up table can provide a selection of different defined generators 80 and the control circuit C can be used to provide the appropriate settings, automatically or for manual adjustment. The generator 80 may optionally be provided as a custom generator with the tool 10 or made available from an authorized supplier according to defined specifications of operation to meet regulatory guidelines for medical use and comply with Good Manufacturing Practices, for example.

Figure 7C:
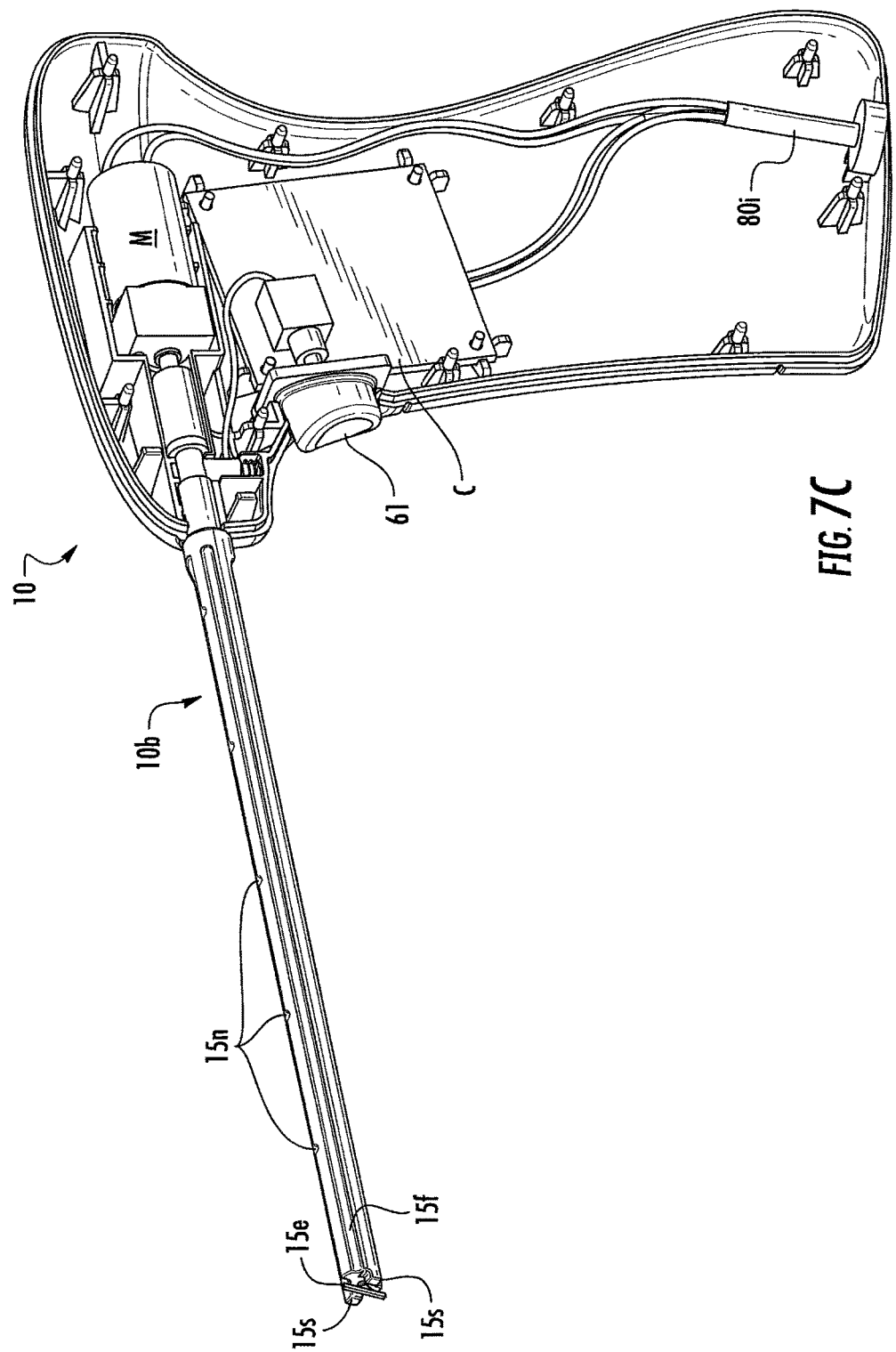
FIG. 7C is a partial cutaway view of another embodiment of a surgical tool with the cautery and tissue scraping end according to embodiments of the present invention.
Figure 8A:
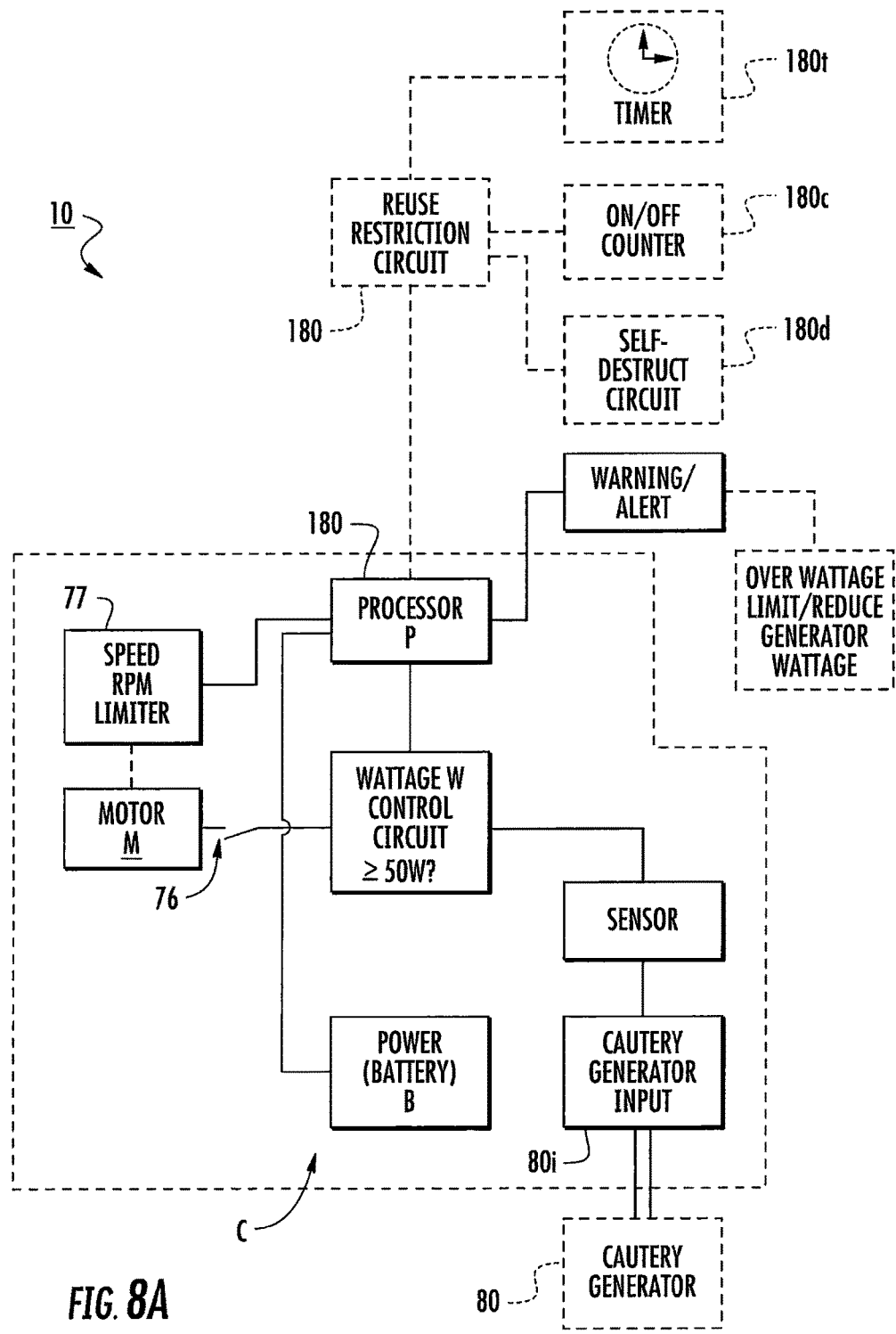
FIG. 8A is a schematic illustration of a circuit according to embodiments of the present invention.
Figure 8B:
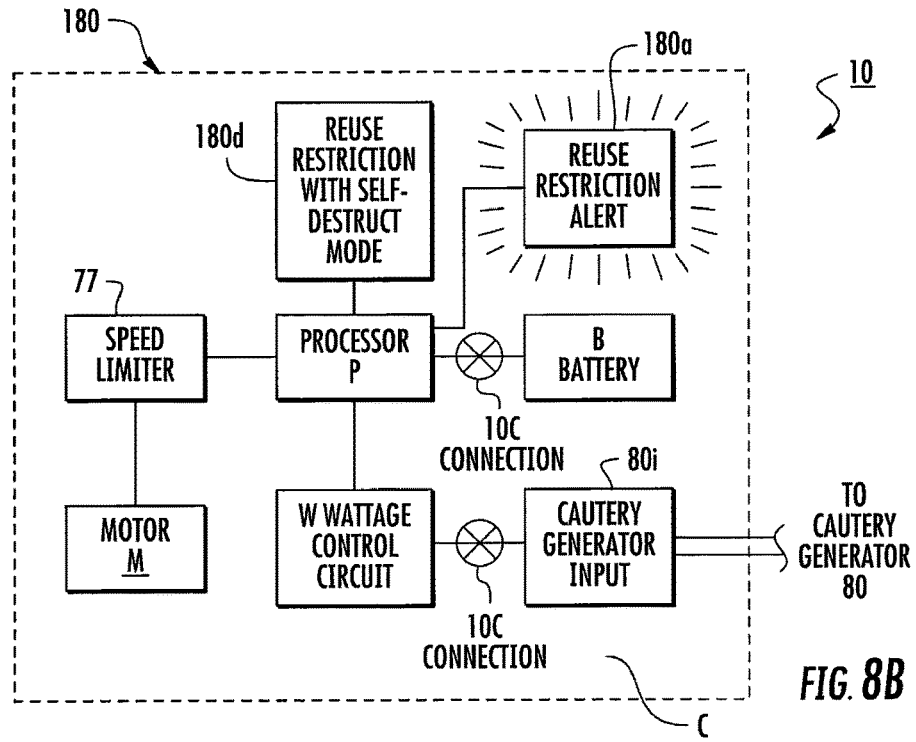
FIG. 8B is a schematic illustration of a circuit with a reuse restriction circuit that can self-destruct certain components according to embodiments of the present invention.
Figure 8C:
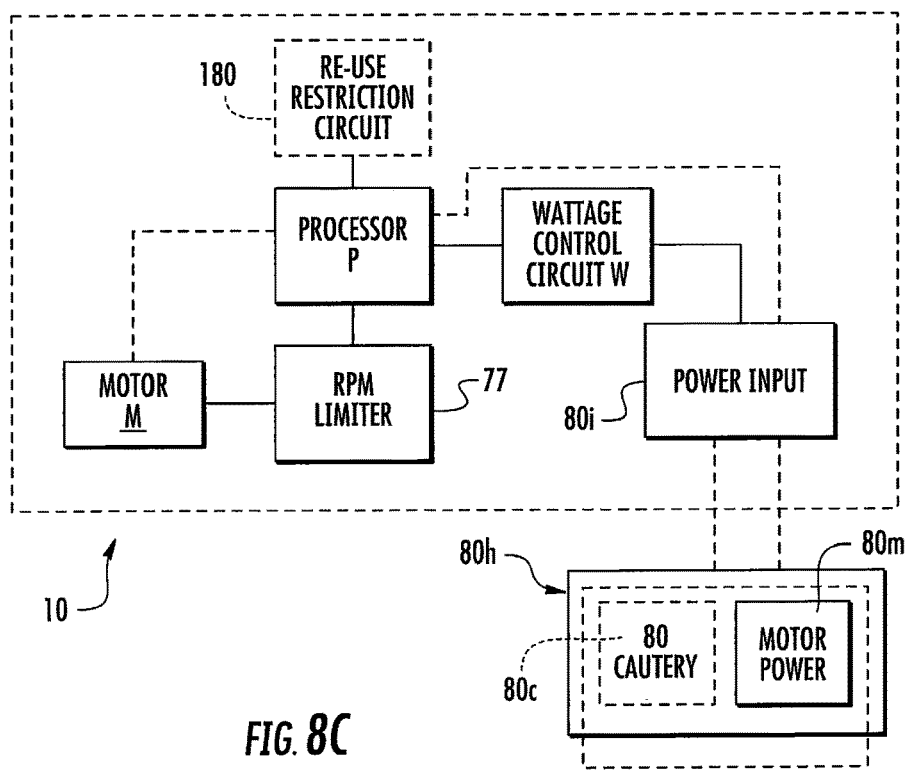
FIG. 8C is a schematic illustration of a circuit with a combination cautery and motor power source according to embodiments of the present invention.

As shown in FIG. 8C, in some embodiments the cautery generator 80 can be provided in a combination unit or housing 80h that also holds the motor power source 80m so that the tool 10 can have an electrical connection to the combination unit for powering both functions during a medical procedure. The unit 80h can thus provide cautery power to the surgical tool 10 and electrical power to the tool 10 for the rotational motor M of the device shaft or barrel. Having the generator unit 80h provide both the cautery and electrical power generation/input 80i (FIG. 7C) can eliminate the batteries for powering the rotational motor, e.g., batteries are not required to be held onboard the body of the tool.

During a procedure, typically during or after a defined active cauterizing time, e.g., between about 10-30 seconds of active cauterizing time, with an exemplary cautery site temperature of about 302 degrees F., the vacuum port 40v, cooperating with the guide cannula 30, can be configured to vent heat H from inside the guide tube 30 (e.g., the lumen 30l) outside the patient body and maintain a maximum temperature inside the guide cannula 30 to be at about 122 degrees Fahrenheit (degrees F.) (e.g., no greater than +2 degrees) or lower, e.g., typically below 122 degrees F. and at or above about 80 degrees F. Animal laboratory testing or cadaver testing can be used to test the max temperature using the vacuum port 40V on the tubular support member 40 and cooperating guide tube 30 with the cauterizing surgical tool 10. By way of comparison, temperatures inside the lumen 30l of a guide tube 30, held by a tubular support member 40 (without the vacuum exhaust 40v that is in fluid communication with the lumen 30l) during cauterization with a temperature at the cauterization site at about 300 degrees F. can reach temperatures above 122 degrees F., more typically about 140 degrees F. The target temperature for humans (away from the cautery site) is under 124 degrees F., such as between 80-124 degrees F., between 80-123 degrees F. or between 80-122 degrees F.

Figure 3:
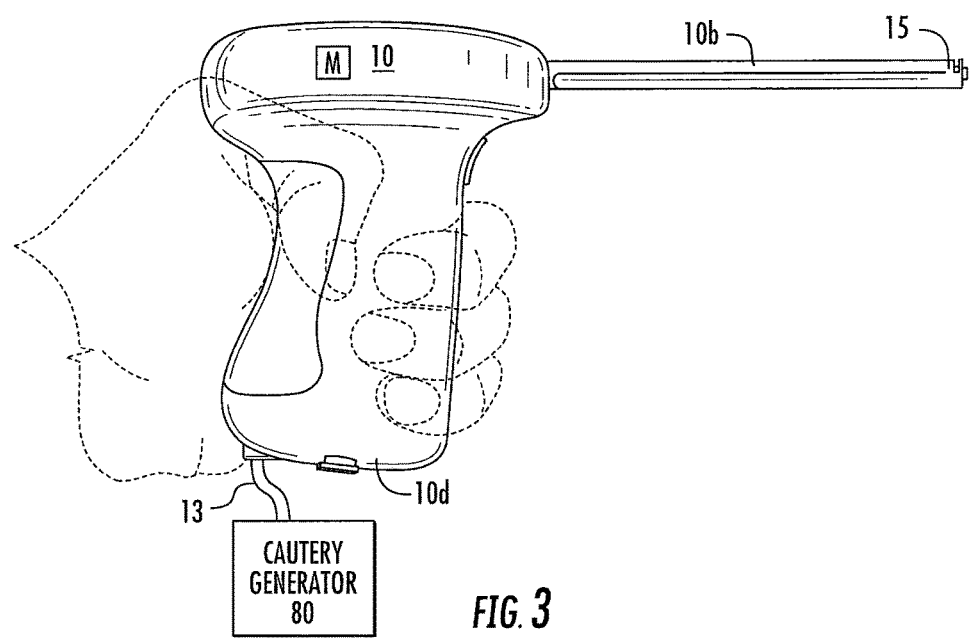
FIG. 3 is a side view of a surgical tool for spinal facet pain alleviation therapies according to embodiments of the present invention.

FIG. 3 illustrates a tool 10 with the barrel 10b which is rotated by an onboard motor M powered by either at least one battery (shown as a set of batteries pack B, FIG. 7A) or a DC or AC power source (FIG. 7C) that is remote from the tool 10 such as in a unit housing 80h with the electrosurgical cautery generator 80c (FIG. 8C).

The tool 10 can include a cord 13 that connects to the (cautery/and or power) generator 80. The tool 10 can have a pistol grip 10p with a latch 10d that allows a user to easily detach or remove the batteries as a pack (where batteries area used) so as to be single-use engineered.

The tool 10 can also be configured with a circuit C (FIGS. 8A-8C) that automatically destroys components to inhibit reuse.

Referring to FIGS. 4A-4D, 9A, 9C, 10A, 15A, 17A and 18A, for example, the heat exhaust ports 30p can be longitudinally spaced apart along a length of the guide cannula 30. Although shown as vertically aligned, they may be laterally offset and may be clustered rather than regularly spaced apart. Also, although shown as a plurality of ports 30p, the guide cannula 30 may include a single port 30p.

Figure 4D:
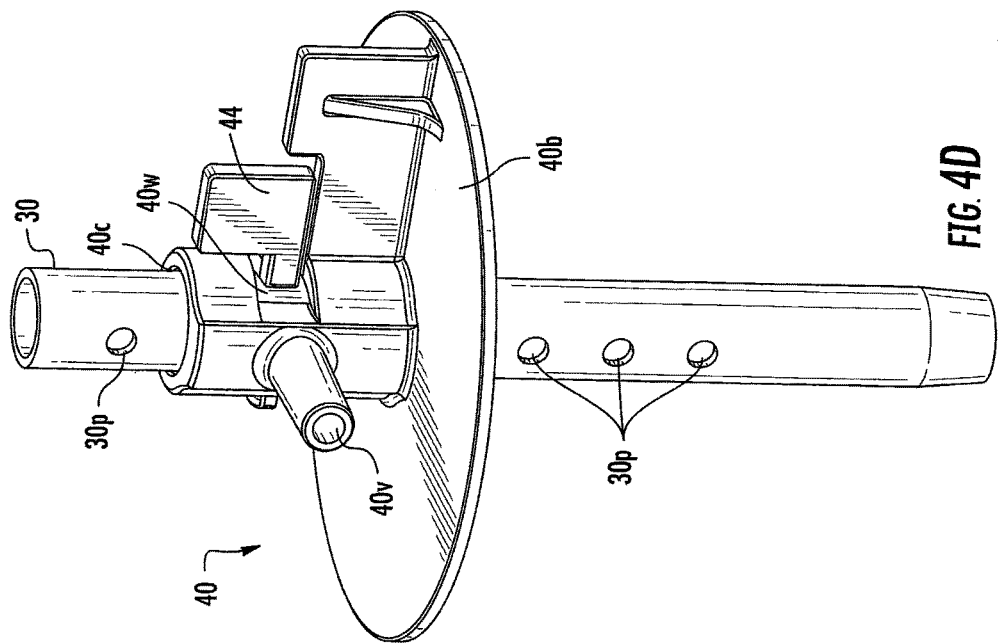
FIG. 4D is a corresponding enlarged side perspective view of the device shown in FIG. 4C.
Figure 4C:
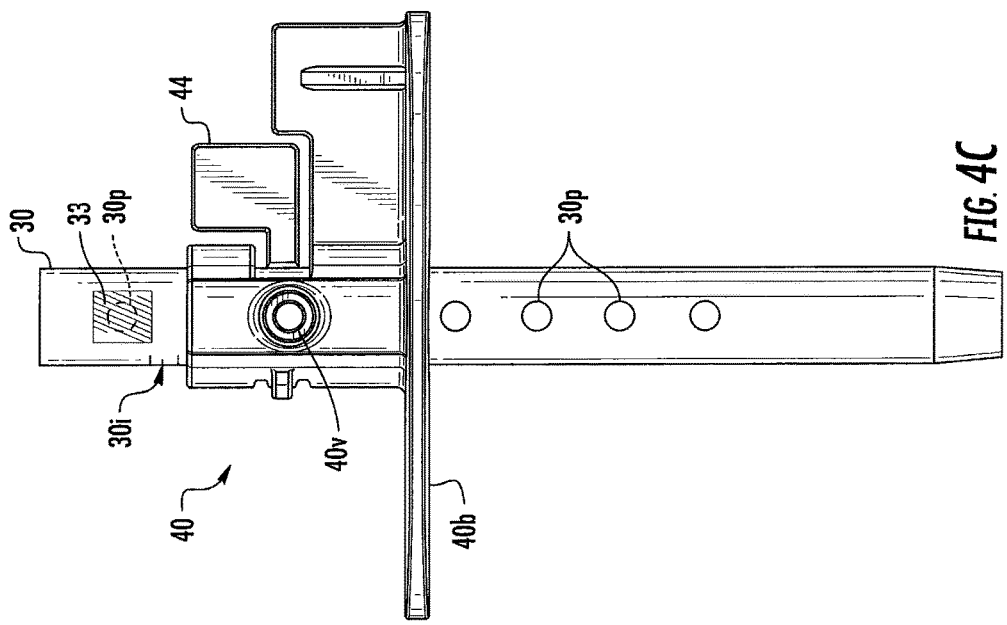
FIG. 4C is a front view of the device shown in FIGS. 4A and 4B but with the tubular member shown in solid.
Figure 12:
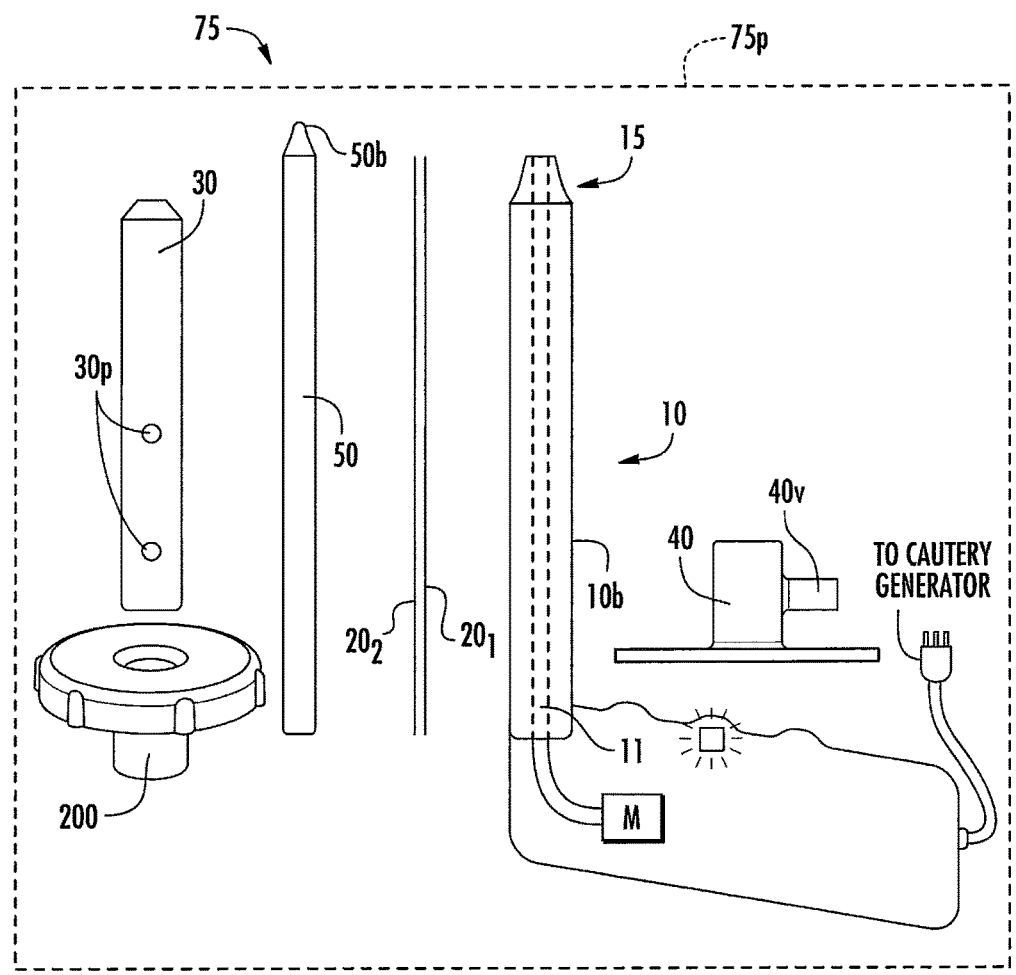
FIG. 12 is a schematic illustration of a kit for spinal facet surgical procedures to alleviate pain according to embodiments of the present invention.

Referring to FIGS. 4C and 5A, in some embodiments, the ports 30 may be provided in a closed state prior to user selection of a desired port or ports for a particular procedure or patient. The ports 30p may include a sealant or cover 33 (FIG. 5A) that is thermally suitable that attaches to an inner and/or outer wall of the guide cannula 30 and extends over one or more of the ports 30p. The ports 30p may be preferentially scored 30s as shown in FIG. 4C, but intact so as to be sufficiently sealed to inhibit gas exhaust when intact. The ports 30p can be substantially or totally sealed with thinner wall perimeter segments that can be detached to expose a port 30p to allow a user to push open a desired port 30p during or prior to a procedure. FIG. 5B illustrates that where a cover 33 is used, the cover 33 may be pierced, punctured or pushed open using a shaped end 40e of a movable arm of the vacuum port 40v. FIG. 5C illustrates a separate tool 41 that can be inserted directly into a port 30p or into the arm of vacuum port 40f to reach the cover 33 over a desired port 30p may be included in the surgical tool kit 75 (FIG. 12).

FIG. 5D illustrates that a cover or seal (e.g., a cap) 42 can be attached to the vacuum port 40v. The cap 42 can also or alternatively be attached to a body 41 with an end 42e that can push, pierce or otherwise open the port 30p or the cover 33 over a desired port 30p. A user can select and open a port 30p that is at a height that is appropriate for use for a particular procedure (e.g., depending on the height of the guide cannula relative to the tubular member 40).

It is preferred, but not required, that the port 30p that is used for a procedure align longitudinally and laterally with the vacuum port 40v. However, the ports 30p, 40v may be misaligned as long as there is sufficient fluid communication to provide for heated exhaust gases to be removed to keep the temperature in the guide cannula 30 (at least the part that is in the patient body and proximate the skin S) at 122 degrees F. or below without requiring other active cooling inputs.

Figure 6A:
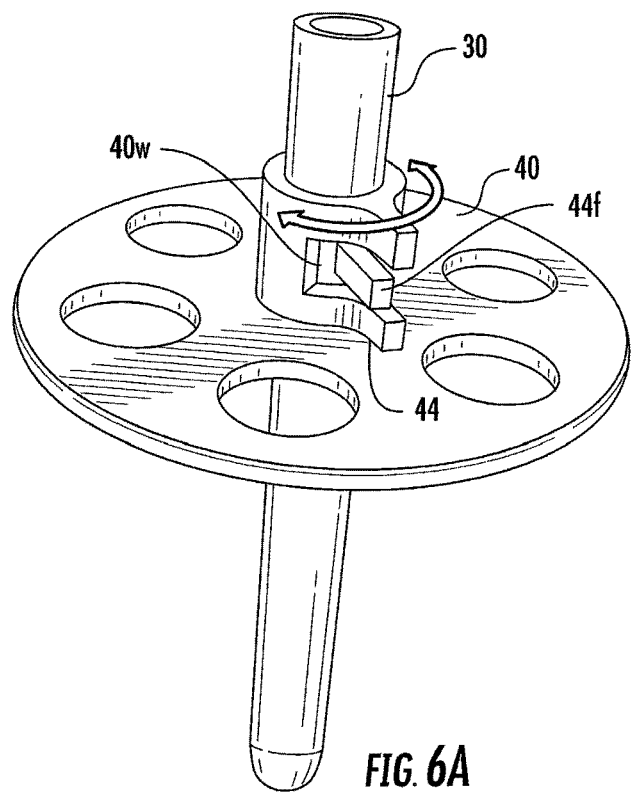
FIG. 6A is a side perspective view of a tubular support member and tube configuration according to embodiments of the present invention.
Figure 6B:
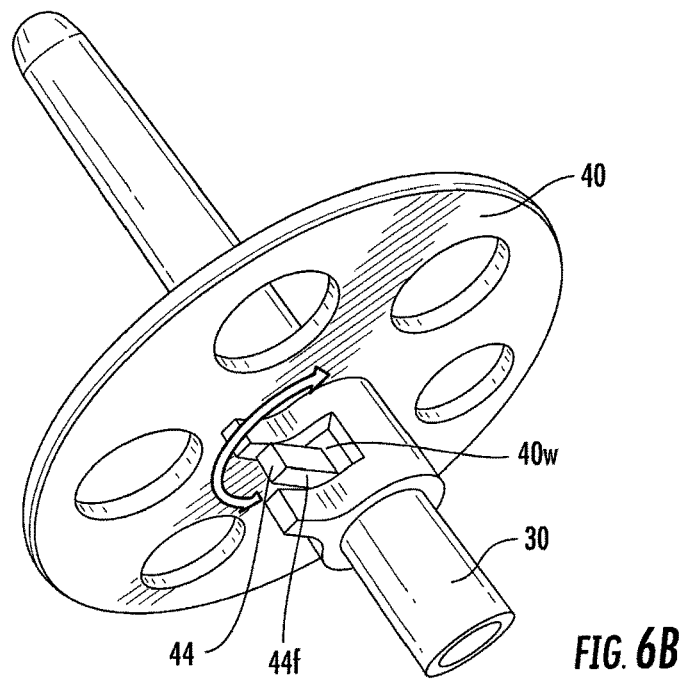
FIG. 6B is an end perspective view of the device shown in FIG. 6A.

FIGS. 6A and 6B illustrate the height adjustment/lock member 44 can include a finger 44f, that can flex back and forth in a direction that can be perpendicular to the long axis of the guide cannula 30 to selectively release and lock the guide cannula 30 at a height position as indicated by the arrow. FIGS. 6A and 6B also show that the base 40b can have a light weight configuration with a plurality of spaced apart apertures 40a. Although shown as circumferentially, regularly spaced apart according to some embodiments, the apertures 40a can be configured with other geometries and may be irregularly spaced apart. The apertures 40a can be provided as 6 (six) relatively large apertures as shown, lesser apertures (not shown) or a more dense number of smaller apertures (also not shown).

Figure 7A:
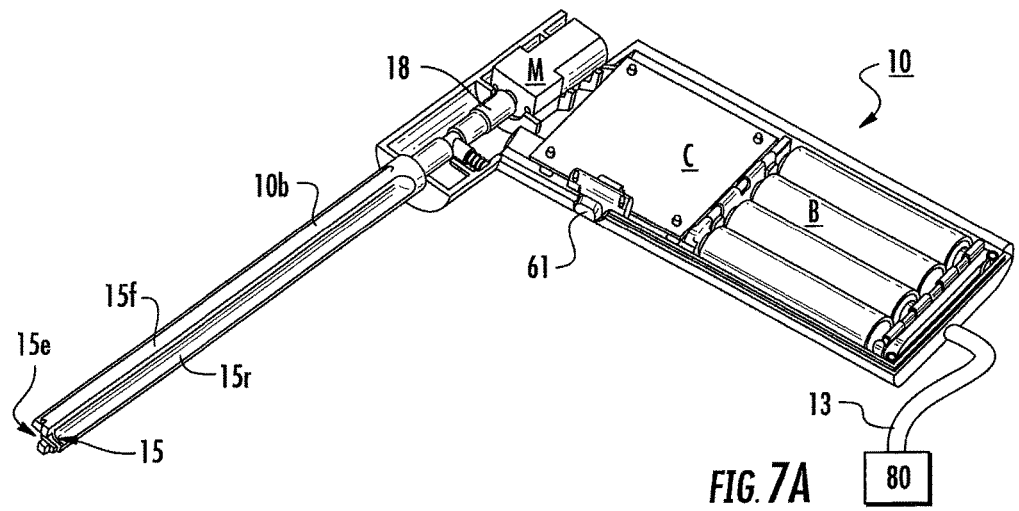
FIG. 7A is a partial cutaway top perspective view of a surgical tool according to embodiments of the present invention.
Figure 7B:
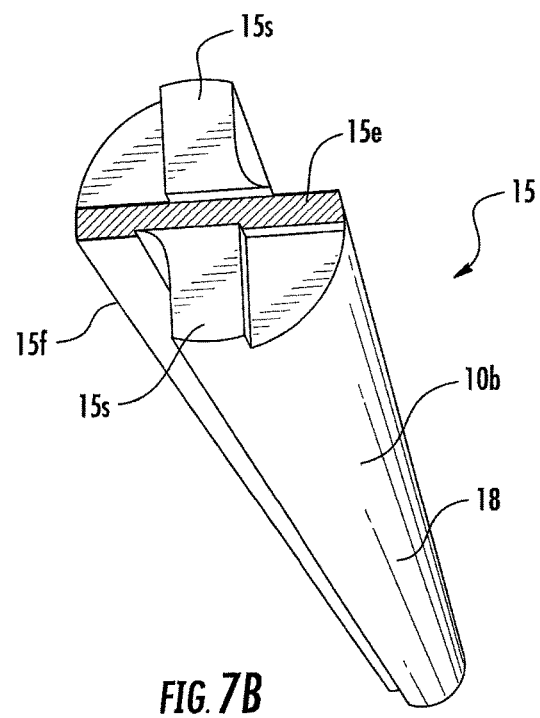
FIG. 7B is an end perspective view of a shaft with a surgical cautery and tissue-scraping tool head according to embodiments of the present invention.

FIGS. 7A and 7C illustrate that the tool 10 can have an onboard control circuit C with a user activation input (shown as a push button) 62. The electric motor M turns the shaft 18, which turns the barrel 10b and rotates the barrel with tissue scraping elements 15s and cautery element 15e on the head 15.

The circuit C can include at least one processor P that controls operational parameters of the device 10 and/or can monitor for defined inputs such as a defined wattage range of a cautery generator 80. In preferred embodiments, the maximum wattage of the cautery/electrosurgical generator 80 is between about 40 Watts to about 60 Watts, which is much less than maximum wattages that many surgical cautery generators can provide. Thus, the circuit C can be configured to prevent operation, disable operation, turn power off to prevent heating and/or rotation, and optionally send a warning or alert to a user to adjust the wattage if the wattage is above the defined limit, e.g., 40 Watts, 50 Watts or 60 Watts, with a power curve having a maximum output wattage of between 150V-230V, e.g., 150V, 160V, 170V, 180 V, 190V, 200V, 210V, 220 V or 230V and a peak maximum current of 1000 mA.

Figure 8D:
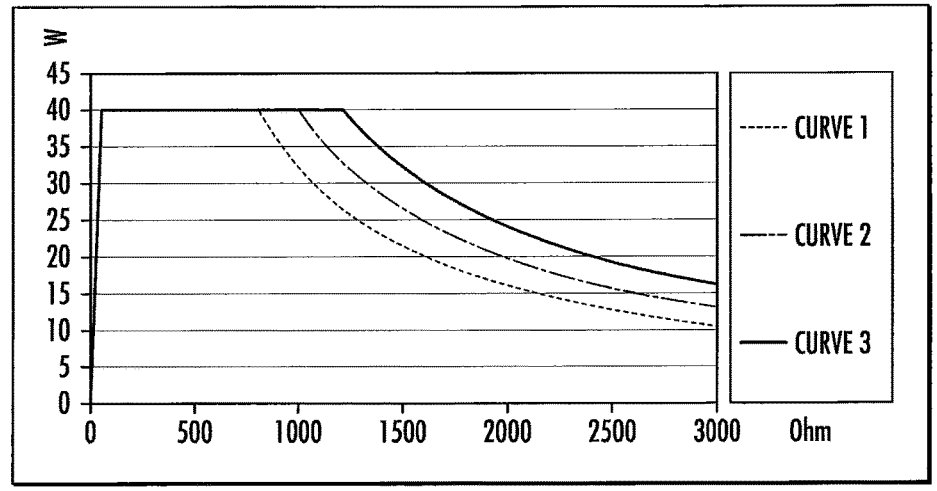
FIG. 8D is a graph of exemplary power curves that an electrosurgical (RF power source) generator can employ according to embodiments of the present invention.

As shown in FIG. 8D, in some embodiments, the cautery generator 80 can provide the cautery output to the tool 10 using a defined power curve. The graph illustrates three exemplary power curves. The operational power curve can have a maximum voltage of 180 V, 200V or 220V, a maximum current of about 1000 mA and a maximum output wattage of 40 W over 0-3000 Ohms. The cautery output can be monopolar, in some embodiments.

The electrosurgical generator 80 can employ a Field-Programmable Gate Array (FPGA) algorithm for controlling the RF output of the electrosurgical generator 80 for the surgical tool 10. The generator 80 may use an FPGA algorithm with a power curve with defined maximum values of power, voltage, current. FPGA controls are well known, see, e.g., U.S. Pat. No. 6,142,992, the contents of which are hereby incorporated by reference as if recited in full herein.

In some embodiments, the circuit C can be totally onboard the tool body 10b, totally onboard the cautery generator unit 80 or distributed between the tool body 10b and the generator unit 80. The circuit C may be distributed in remote devices using an intranet and/or the internet such as a remote server in a distributed network such as a CLOUD-based network.

FIG. 8A illustrates an example of an onboard circuit C that can have at least one processor P (which can include a digital signal processor), a wattage control circuit W in communication with the cautery generator input 80i which can include a sensor 80s that can be monitored by the circuit W. The processor P can control a switch 76 that deactivates the tool 10 and/or turns off or inactivates power to the motor M. The processor P can send a warning to an onboard or remote display or an audile alert to allow a user to adjust the cautery generator wattage setting if the wattage is above a defined limit, typically above 50 Watts. This control may allow for use with a number of different conventional cautery generators in different clinics or hospitals and/or in different countries.

In some embodiments, the head 15 can have an electro-conductive member 15e and/or outer surface to which electrical energy is supplied (in bipolar or monopolar mode), thereby permitting the head 15 to cauterize tissue. The electro-cauterization can be any suitable cautery source, typically RF power, although other electrical sources may be used. For additional discussion of components of a suitable combination spinal facet debrider tool 10, see, e.g., U.S. Pat. No. 8,167,879; and co-pending U.S. patent application Ser. No. 14/257,490, the contents of which are hereby incorporated by reference as if recited in full herein.

The distal end portion of the therapy delivery tool 10 with the head 15 can have a maximal outer diameter that is between about 5-15 mm, such as about 5 mm, about 6 mm, about 7 mm, about 8 mm, about 9 mm, about 10 mm, about 11 mm, about 12 mm, about 13 mm, about 14 mm and about 15 mm, typically between 10-12 mm.

The procedure can be done via conscious sedation and local anesthesia or general anesthesia as per the surgeon's and patient's preference. For, example, conscious sedation can be used with a remifentanyl mixture. The spinal region is typically prepped and draped accordingly. Utilizing fluoroscopic or other suitable imaging guidance, the facet joints J that may be treated can be identified.

To facilitate a minimally invasive treatment, a semi-rigid or rigid guidewire and/or pin 20 (e.g., a Steinman pin)(FIG. 12) with a diameter of approximately 1 mm can be inserted through skin S and tissue of a patient into the target facet joint region. The guidewire/pin 20 can be tapped into place with a small hammer or other suitable device. A small incision, typically between about 0.25-1 inch, e.g., about ½ inch or about ¾ of an inch can be made about the pin 20. In other embodiments, the incision can be made before or during the insertion of the pin 20.

Figure 10A:
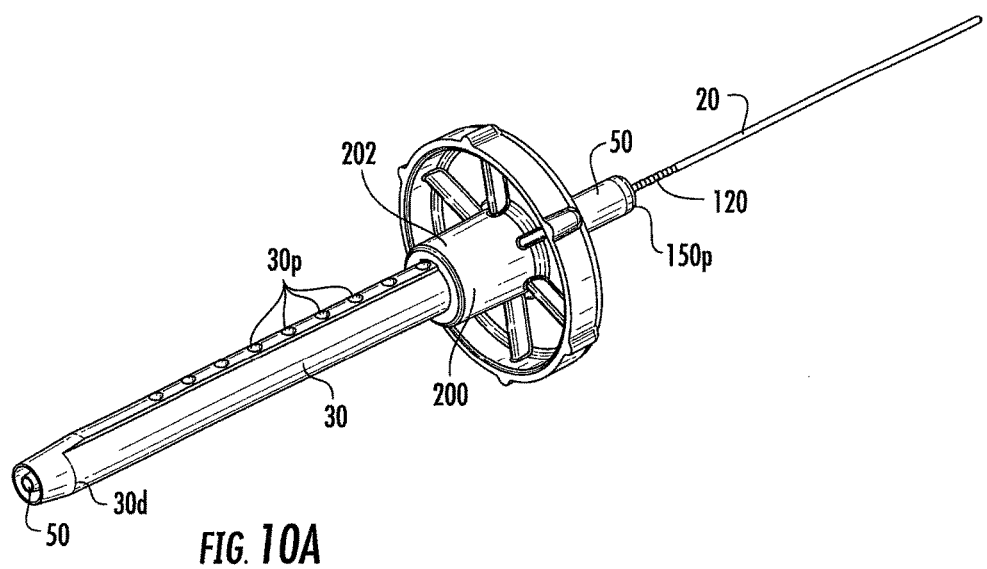
FIG. 10A illustrates the sub-assembly shown in FIG. 9A used with a dilation tube and k-wire according to embodiments of the present invention.
Figure 10B:
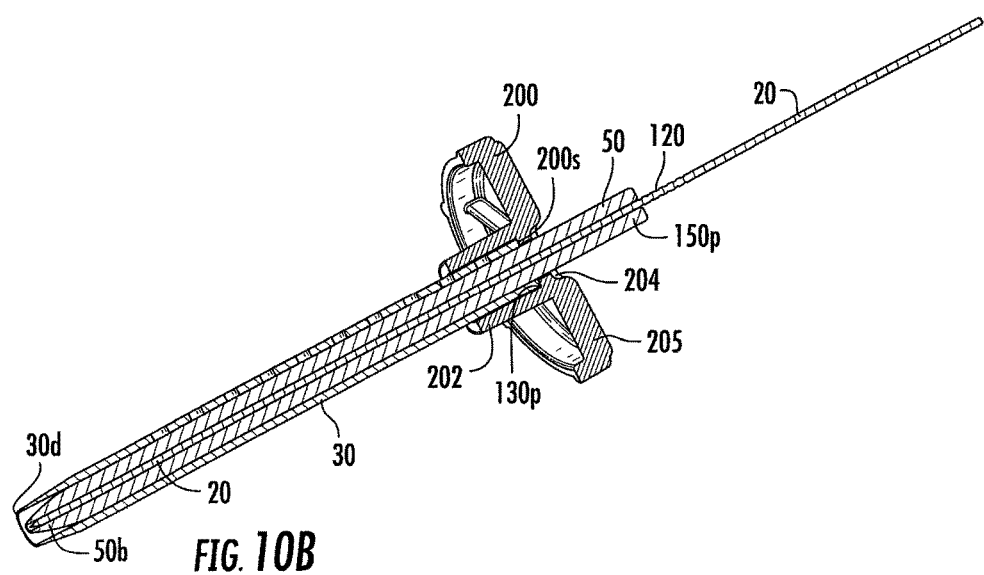
FIG. 10B is a section view of the cooperating components shown in FIG. 10A.

The guide cannula 30 (sometimes also called "a working cannula", "working portal" or "portal" as discussed above) can be inserted into the patient so that a distal end thereof 30d (FIG. 1) resides proximate the target facet site J (FIG. 2). The guide cannula 30 can be inserted over the guide pin 20 to help position the guide cannula 30 in the body. Typically, as shown in FIGS. 10A and 10B, the guide cannula 30 is inserted over a dilation tube 50 which is first inserted over the guide pin or wire 20.

The (external) tubular member 40 holds the guide cannula 30 in position. The guidewire/pin 20 and dilation tube 50 may be removed before or after placement of the tubular member 40.

In some embodiments, as shown in FIGS. 9A, 9B, 9D, 10A, 10B, 11A, 11B, 14F, 14G, 15A, 17A and 18A, a hand grip member 200 (sometimes also called "portal driver") can be attached to the guide cannula 30 to cause the distal end of the guide cannula 30d to cut through adjacent tissue thereunder to be able to have the distal end of the guide cannula 30d remain at the joint J (FIG. 2) even when the pressing force from the hand grip member 200 is removed. That is, when just inserting a guide cannula 30 to the location J over the dilation tube 50, the underlying tissue may have sufficient resiliency to resist the placement of the distal end of the guide cannula 30d so as to "reset" or relocate the location of the distal end of the guide cannula to be about 2-20 mm from a bone surface of the target J when the guide cannula 30 is merely pushed into a target position over the dilation tube 50 and/or pin 20. To assure proper and close placement of the distal end of the guide cannula 30, a user can manually rotate and press inward against the hand grip member 200 to thereby cause the distal end of the guide cannula 30 to cut through the tissue proximate the joint J. This action may be carried out while a user also presses down against the tubular member 40 to retain a desired aligned position.

Typically, once the distal end of the guide cannula 30 is proximate a target site (e.g., within 0.001 mm to about 5 mm of the bone at the joint J), a user grips the member 200 while concurrently pushing and rotating the member 200 to carry out the desired placement of the distal end of the guide cannula 30d. There is no need to twist the hand grip 200 while pressing against it for an entire insertion length. Also, the amount of pushing force applied by a hand of a user while twisting the hand grip member 200 is relatively low and easily manually applied, typically the pressing force is in a range of about 5 to about 50 Newtons. It is also contemplated that the twist can be in a single direction and less than one revolution to place the device 30d.

Figure 9A:
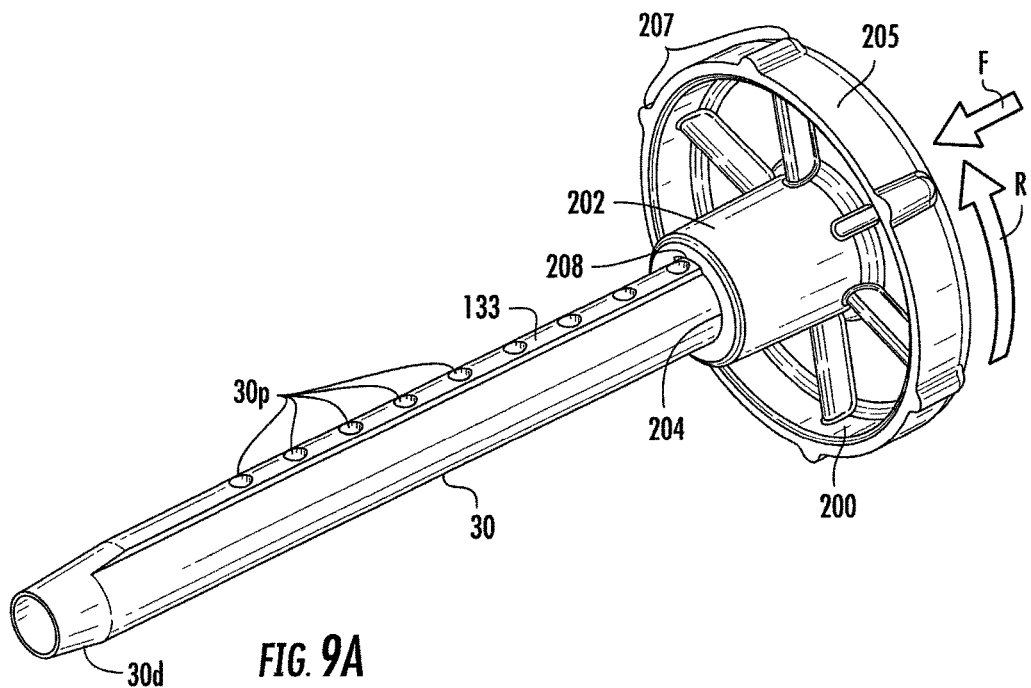
FIG. 9A is an enlarged side perspective view of a sub-assembly of a working tube (guide cannula) with a cooperating hand grip member attached thereto according to embodiments of the present invention.

Referring to FIGS. 9A, 9B, 10A, 10B, 11A and 11B, the hand grip member 200 can allow a user to apply an inward force F concurrently with a rotation R as indicated by the arrows in FIG. 9A. In some embodiments, the hand grip member 200 can be releasably affixed to an outer end portion of the guide cannula 30. In some embodiments, the member 200 can be detached from the guide cannula 30 and may be removed before placing the tubular support member 40. In some embodiments, the hand grip member 200 can remain in position and cooperate with the member 40 during a surgical procedure. In some embodiments, the hand grip member 200 may be an integral part of the guide cannula 30.

Figure 11A:
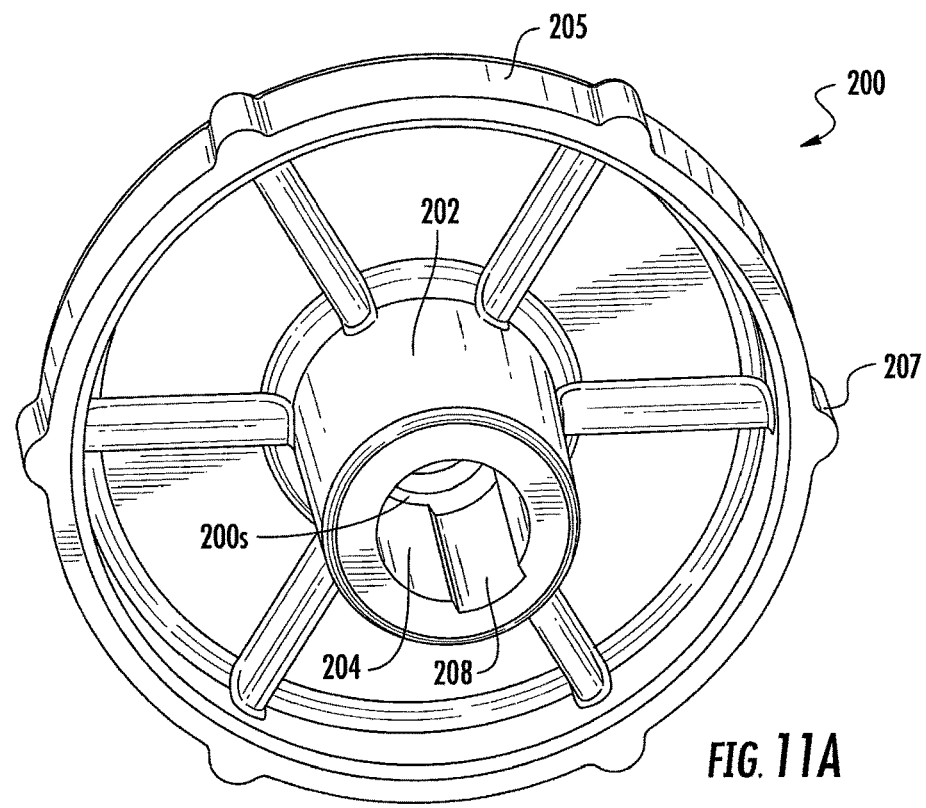
FIG. 11A is an enlarged view of an exemplary hand grip member according to embodiments of the present invention.
Figure 11B:
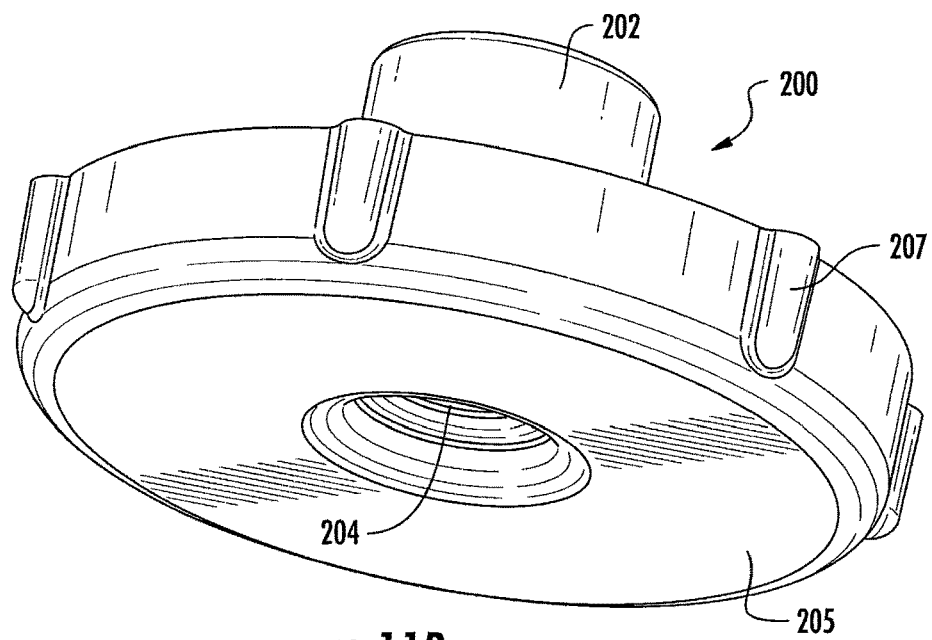
FIG. 11B is an enlarged view of an opposing side of the hand grip member shown in FIG. 11A.

As shown in FIGS. 9A, 9B, 11A and 11B, for example, the hand grip member 200 can have a tubular portion 202 with a cylindrical channel 204 that snugly slidably receives an upper end portion of the guide cannula 30. The channel 204 can be a through-channel as shown in FIGS. 10B and 11A, for example.

The hand grip member 200 can have a hand-grip portion 205 that resides above the tubular portion 202 and that has a larger radial extent than the tubular portion 202. The hand grip portion 205 can be substantially circular, typically with a diameter that is greater than that of the guide cannula 30, such as between 2× and 5× greater than the diameter of the guide cannula 30. The hand grip portion 205 may include an outer perimeter with spaced apart protrusions 207 that can provide finger grip features and/or anti-slide surfaces. The cylindrical channel 204 can have an interior circumferentially extending stop 200s that resides between opposing upper and lower portions of the channel 204, typically below but adjacent the hand grip 205. The proximal end of the guide cannula 130p can abut against the stop 200s as shown in FIGS. 9B and 10B.

Figure 9B:
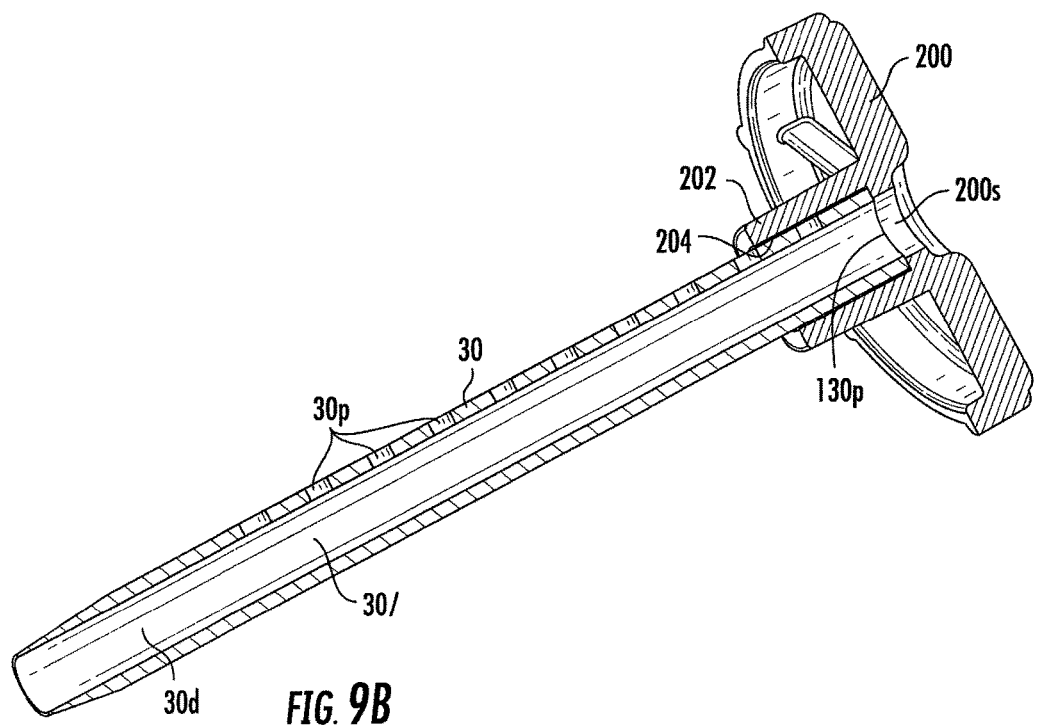
FIG. 9B is a section view of the sub-assembly shown in FIG. 9A.
Figure 9C:
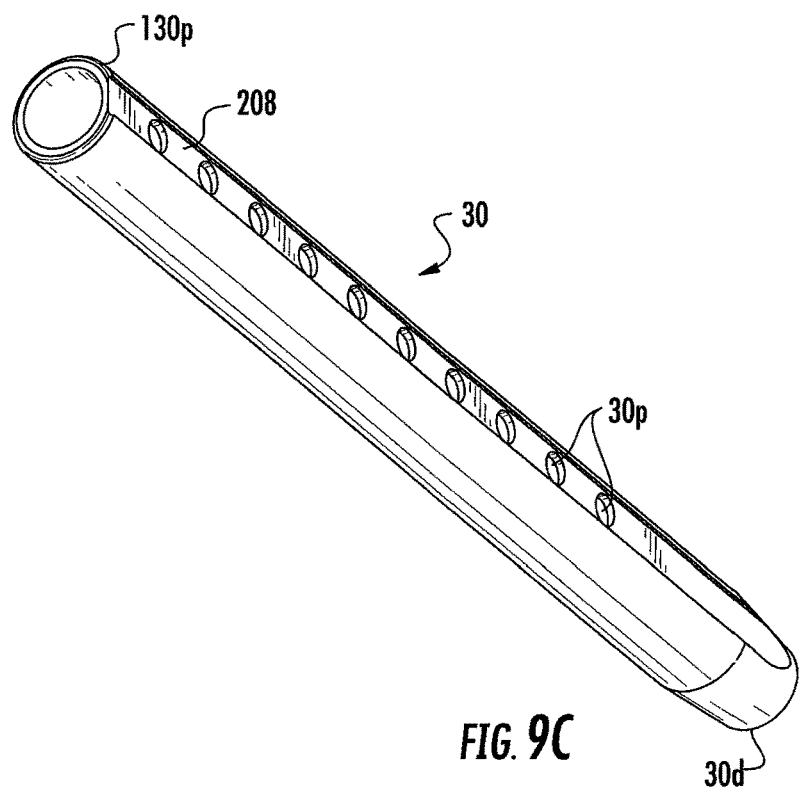
FIG. 9C is an enlarged side perspective view of another embodiment of a working tube (aka, working portal or guide cannula) according to embodiments of the present invention.
Figure 9D:
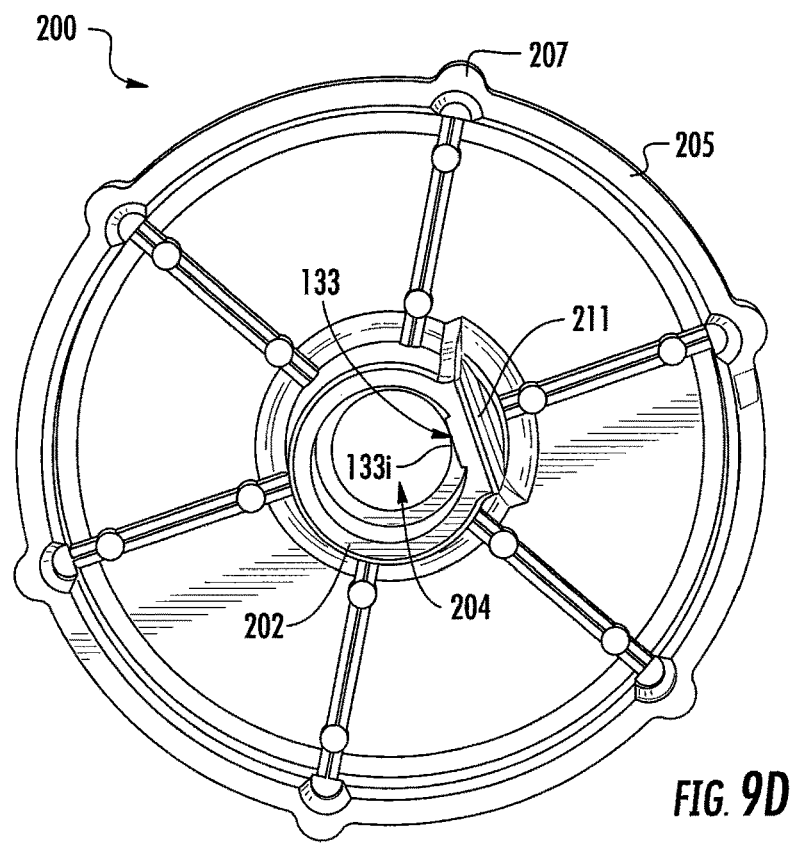
FIG. 9D is an enlarged top view of another embodiment of a hand grip member according to embodiments of the present invention.

As also shown in FIGS. 9A and 9B, the tubular portion 202 of the hand grip member 200 can have an inner wall with at least one longitudinally extending recess 208 that matably receives a corresponding longitudinally extending protrusion 133 on the outer wall of the guide cannula 30, which may optionally hold the exhaust ports 30p. The opposite configuration may also be used, e.g., the inner wall of the tubular portion 202 can have the protrusion 133 while the guide cannula outer wall can have the recess 208 as shown in FIGS. 9C and 9D or combinations of these or other configurations that allow the fixation for rotation of the guide cannula 30 with the hand grip member 200. Where the guide cannula 30 has the longitudinally extending recess 208, the ports 30p can be placed, spaced apart, within this recess 208. FIG. 9D also illustrates that the male key 133 can face inward into the channel 204 and can reside opposite a flat segment 211 laterally spaced apart a distance of between 0.01 inches and 0.25 inches from the inner surface of the key 133i. Referring to FIGS. 1 and 9E, the tubular support member 40 can include a longitudinally extending open channel 40c with an inner wall 40i that can comprise at least one key feature 40k that can engage the key feature 208 and/or 133 of the guide cannula 30. Where the guide cannula 30 has the protrusion 133 (FIG. 9A), the key feature 40k of the tubular support member 40 can comprise a recess (FIG. 1) and where the guide cannula 30 has the recess 208, the key feature 40k can comprise a protrusion (FIG. 9E). The key feature 40k can extend aligned with and above and/or below the vacuum port 40v to position a port 30p to face the vacuum tube 40v. The key feature 40k may alternatively be offset from the ports 30p but engage the guide cannula 30 to align a respective port 30p with the vacuum tube 40v.

As shown in FIGS. 10A and 10B, the hand grip 200 can be attached to the guide cannula 30 and receive a k-wire or pin 20 as well as the dilation tube 50 in the channel 204. The proximal end 130p of the guide cannula 30 can reside under the hand grip 205 with the proximal end 150p of the dilation tube 50 above as shown. In other embodiments, the guide cannula 30 can extend through the hand grip 205 and reside above the hand grip 205 along with the dilation tube and guide-wire or pin 20 (FIGS. 10A, 14A-14F). Typically, at least the k-wire or pin 20 remains in the guide cannula 30 as a user rotates and pushes against the hand grip member 200 to cut through tissue to position the guide cannula distal end 30d at the target site J so that it remains there upon removal of the force applied to the hand grip member 200 and/or removal of the hand grip member 200 from the guide cannula 30 (for detachable versions). The tubular support member 40 can be positioned on the guide cannula 30 after it is in proper position or before or during. In some particular embodiments, the hand grip member 200 can be detached from the guide cannula 30, then the tubular support member 40 can be placed on the patient and attached to the guide cannula 30.

FIGS. 10A and 10B also illustrate that the k-wire or pin 20 can include visible markings 120 for a visual reference that a user can see to align with a top or proximal end of the guide cannula 130p and/or dilation tube 50. As the k-wire or pin 20 touches bone at the target treatment site J, assessment of position of the distal end of the guide cannula 30d and/or dilation tube 50 can be made relative to the visible markings 120. The visible markings 120 can be striations, notches, embossments, color markings, graduated measurement indicia marks or combinations of same. The upper end portion of the dilation tube 50 may be visually transmissive, such as translucent or transparent. The upper end of the dilation tube may also include visual reference indicia markings (not shown).

The tubular support member 40 can be configured to provide a depth stop for the therapy delivery tool 10 and optionally structural, such as rotational stabilization for the tool barrel 10b proximate the skin entry site S. The tubular support member 40 can slidably receive and releasably hold the guide cannula 30 and tool barrel 10b and may be used without requiring the guide pin 20, e.g., the guide pin 20 may not be used or may be withdrawn prior to or after the member 40 is in position on the patient while holding the guide cannula 30 at a desired stop depth.

As shown in FIGS. 1, 2, 4A-4D and FIGS. 15A, 17A and 18A, the tubular support member 40 can have a base or bottom 40b that resides against skin S of the patient, either directly or indirectly. The base or bottom 40b can have a maximal width W of between about 2-6 inches, typically between about 3-5 inches, such as about 3 inches, about 3.5 inches, about 4 inches, about 4.5 inches and about 5 inches. The base or bottom 40b can have a larger width than the width of the tube 40t which has a through-channel 40c for the guide cannula 30 and/or tool 10. The tube 40t typically has a smaller height than the height of the barrel 10b (FIG. 12) of the therapy delivery tool 10 and/or height of the guide cannula 30. In some particular embodiments, the tubular support member r 40 can have a maximal height that is between about 2-10 inches, typically between about 3-6 inches, such as about 3 inches, about 3.5 inches, about 4 inches, about 4.5 inches, about 5 inches, about 5.5 inches, and about 6 inches, although t other height dimensions may be used.

As shown in FIGS. 1, 2, 4A-4D, 15A, 17A, and 18A, the tubular support member 40 can releasably, slidably engage the guide cannula 30. The member 40 can be configured with the height adjustment member 44 configured to releasably lock against the outer surface of the guide cannula 30. The member 44 can provide the locking engagement 44 using a physical lock member (e.g., a clamp or other suitable lock) or a locking configuration, e.g., frictional engagement or other locking configuration. The tubular member 40 and cannula 30 engagement can be through any suitable physical engagement that allows the member 40 to lock against the cannula 30 directly or indirectly and preferably also allows for the height adjustment of the cannula 30 in the tubular member 40.

The therapy device 10 can be configured such that when the elongate barrel 10b is inserted fully through the guide cannula 30 in an operative configuration, the head 15 and/or distal end of the therapy device 10d extends beyond the front or distal end 30d of the cannula 30 only by between about 2 mm to about 7 mm, such as about 2 mm, about 2.5 mm, about 3 mm, about 3.5 mm, about 4 mm, about 4.5 mm, about 5 mm, about 5.5 mm, about 6 mm, about 6.5 mm or about 7 mm. Thus, the tubular support member 40 locks the cannula 30 in a longitudinal position and the stabilized/locked position of the cannula 30 relative to the skin of the patient S based on the tubular member 40 keeps the distal end 10d of the barrel 10b and/or head 15 at the target site and acts as a stop to keep the head 15 from moving deeper into the body.

As shown in FIG. 2, the top of the guide cannula 30t and a tool interface 10i can cooperate to keep the tool barrel 10b can define a hard stop and keep the tool barrel 10b from moving further inward relative to the cannula 30. The cannula and tool interface 10i can be provided in any suitable configuration. In the example illustrated, the interface 10i is shown based on the shape of the tool and top of the cannula 30t, e.g., through abutting contact to provide a physical interference/stop.

The tubular member 40 may optionally provide some structural support for the guide cannula 30 and/or tool 10 at the entry site. As noted above, the tubular member 40 can have a base or bottom 40b that has a greater width/surface area than the primary (tubular) body thereof 40t. The width of the bottom 40b can be larger than the width of the cannula 30 by between two-ten times, but may be only slightly larger or even the same or thinner in other embodiments. Typically, the bottom 40b has a width that is between about 1-6 inches, more typically between about 3 to about 5 inches. The bottom 40b can be thin, typically between about 1-10 mm, more typically between about 2 to about 4 mm. The bottom 40b can be semi-rigid or rigid. The bottom 40b can optionally be configured to conformably reside against the skin of the patient.

As shown in FIG. 4C, the guide cannula 30 can have visual depth markings 30i, typically in an incremented, graduated scale. The scale can be in microns or millimeters or other defined increments of length position. In some embodiments, the depth indicia marking 30i may be color-coded to reflect shorter versus longer depths or having depth indicia for visual correlation of depths for different treatment levels of the spine.

The longitudinal position of the guide cannula 30 relative to the tubular support member 40 can be adjustable to allow a clinician to adjust for a specific patient and/or target joint to thereby adjust the intrabody depth of the therapy tool delivery head 15 once inserted into the guide cannula 30 that is locked into its desired position by the tubular support member 40.

In some embodiments, a dilation tube 50 (FIGS. 10A, 10B, 12) can be fed over the guide pin 20, typically after the guide pin distal end is anchored to the treatment site of the facet joint J. The dilation tube 50 can be configured with a plurality of cooperating components including an inner tube with a distal end having a tapered end (e.g., a bullet-like shape). The tapered (bullet shaped) end can be inserted down to the facet joint J. The tapered end 50b can be sized and configured to push through the muscle to create an opening, preferably without cutting the muscle.

Optionally, the cannula 30 can slidably extend and reside over the dilation tube 50. The cannula 30 may be sized and configured to snugly reside against the tube 50 so that it does not freely slide along the tube 50 without pushing by a user. The cannula 30 can be positioned upstream of the tapered end on the dilation tube 50 prior to inserting the dilation tube in the body. In other embodiments, the cannula 30 can be separately inserted over the dilation tube 50 after the dilation tube 50 is inserted into the body. In any event, once the tapered end reaches the facet joint J, the guide cannula 30 (e.g., working tube) can be pushed down to the facet joint J so that the distal end 30d of the cannula 30 resides at the facet joint. The dilation tube 50 can then be removed, leaving the cannula 30 in position.

The tubular support member 40 can have an open channel 40c that allows the dilation tube 50 and/or the guide cannula 30 to extend therethrough.

The guide cannula 30 is typically rigid. The guide cannula 30 can be formed or include materials that may be compatible with autoclaving for sterilization. The guide cannula 30 can be metallic or other non-toxic and/or biocompatible material that is sufficiently rigid and that may be high-temperature (autoclave) heat-resistant or suitable for the thermal exposure during cauterization. Other sterilization protocols may be used that do not require heat. The guide cannula 30 can be metallic (and if so can have an electrically insulating material over an end portion or surface thereof) or may be polymeric or other plastic material with sufficient rigidity to provide the guide path for the tool 10. One exemplary material, by way of example only, is Polyether ether ketone (PEEK).

In some particular embodiments, the guide cannula 30 may comprise a stainless steel material with an inner surface having an electrically insulating material. The electrical insulating material can be configured to inhibit arcing with the electro-cautery output, e.g., RF energy at the head 15, when the tool is configured to apply RF energy for the cauterization. The electrical insulating material can be provided by an internal sleeve or coating or otherwise. The insulating material may reside on only a distal end portion of the guide cannula 30 or over an entire inner surface of the cannula 30. The electrically insulating material may optionally reside on the outer surface of the guide cannula 30, such as on the distal end thereof.

It is also noted that the guide pin/wire 20 is optional and that the dilation tube 50 may be inserted without requiring the use of the guide wire/pin 20. Also, where used, the guidewire/pin 20 may extend through the cannula 30 rather than the barrel of the tool 10b and is not required to extend along a centerline of the device 10b, 30. For example, the cannula 30 can have a guidewire channel residing about a perimeter segment.

The tubular member 40 can be positioned prior to, during or after insertion of the guidewire/pin 20 (where used), the dilation tube 50 and/or the cannula 30.

The tool head 15 can be rotated to denude tissue until bone at the target spinal facet joint is reached. In preferred embodiments, the rotation of the head 15 can be automatic using a motor M (FIG. 7A, 7C, 8C) with a drive shaft 18 (FIG. 7A, 7B, 7C) connected to the therapy tool head 15. However, in some embodiments, the denudement head 15 can be manually rotated. The therapy tool head 15 is also configured to cauterize the soft tissue during and/or after the denuding.

As shown in FIGS. 2, 7A, 7B and 7C, in some embodiments, the tool 10 can have an elongate barrel 10b and/or shaft 18 with a length sufficient to reach the target intrabody spinal facet site. The length of the barrel 10b and/or shaft 18 can be between about 100 mm to about 150 mm.

The cannula 30 can have a diameter that is slightly larger than the outer diameter of the shaft 18 and/or tool barrel 10b, e.g., between about 0.1 mm to about 1 mm to allow snug sliding entry of the tool 10. The tool 10 can have various form factors. The barrel 10b may rotate or be static. The barrel 10b can form part of the drive shaft 18 and rotate with the head 15 as an integral or separate component thereof or substantially or totally encase the drive shaft 18 of the rotating head 15.

During use, the proper "stop" for a treatment and/or denuding action can be confirmed by a manual tactile feel since the debrider tool 10 can be made to remove the soft capsular tissue and superficial lining of the joint J but when the bone is reached by the head 15, the tool 10 will not advance or there will be increased resistance and the surgeon can "feel" in a tactile feedback manner that he or she is up against the hard surface of the bone. However, as noted herein, sensors can be used to provide feedback/electronic control.

The denuding of target soft tissue with the tool 10 can have a short duration (with the active rotation of the debridement tool head) that is between about 10 seconds to about 2 minutes long, typically between about 20 seconds to about 40 seconds, on average.

The tool 10 can be configured to continuously rotate the head 15 during both cauterization and subsequent (light) tissue scraping/cleansing upon contact with bone at the facet joint J. In some embodiments, the tool 10 can be configured to discontinuously rotate the head 15 and/or interleave the cauterization with the rotation.

Once the soft tissue is denuded, the tool head 15 can be rotated with sufficient force and time to contact the outer surface of the bone under the denuded tissue for a desired short time, e.g., between about 10 seconds to about 2 minutes, more typically between about 10 seconds to about 60 seconds, to cleanse an exposed outer surface of the bone thereat substantially without removing bone. The short tissue cleansing/scraping time, post-cauterization (e.g., post-denuding), can be controlled with an auto-shutoff for the tool rotation and can be timed based on user or electronic (auto) shut off of the cautery/burn or based on sensor feedback of contact with bone.

The tool 10 can be rotated with the same rotational speed for the bone surface cleansing relative to the denuding action or with a different rotational speed and/or force for the bone surface cleansing relative to the denuding action. In some embodiments, the tool 10 has a first defined rotational speed range for the denuding and a different defined rotational speed range for the cleansing. The transition from denuding (with or without cauterizing) to cleansing can be automatic or manual. If automatic, a sensor can trigger the transition to a different speed and/or to terminate the power to stop the cauterizing action. If manual, a user interface (UI) via a control such as a switch or a voice prompt to a control circuit can direct the change in operation, e.g., slow rotation and stop cautery/burn.

In some embodiments, the tool 10 can be configured to apply the cauterization without rotation of the head 15 then cleanse/tissue scrape with the rotation of the head 15. This may be particularly suitable for laser, ultrasound or cryo-ablation configurations.

As shown in FIGS. 7A and 7C, by way of example only, in some particular embodiments, the different speeds can be selectively applied by the user via at least one user input 61, such as denude and cleanse mode control inputs on the tool 10 that are in communication with the control circuit C and motor M. The inputs 61 may be a single physical input comprising one or more UI 61, such as knobs, buttons, triggers, or GUI inputs on a miniature touch screen display onboard or in communication with the tool 10. The UI can comprise voice-based inputs/commands, e.g., "START DENUDE, START/STOP CAUTERIZE, START/STOP SCRAPE" and the like.

The different speeds for the cleanse and denude modes (where both modes are used) may be automatically applied by the control circuit 50 based on input from the sensor, where used. In some embodiments, the cleanse mode has a 10-100% faster rotation speed than the denude mode while in other embodiments, the cleanse mode has a slower rotation speed (e.g., 10-100% slower) than the denude mode.

The speed of the therapy delivery tool head 15 (e.g., a tissue scraper and cautery head) can be relatively low to avoid cutting into the bone. Most orthopedic burrs will operate up to 60,000 rpm which can be hard to control and can dig into the bone. Thus, lower rotational speeds are desired for the denuding and/or cleanse modes or action. The objective is to sweep the tissue off the bone and not drill into the bone during the cleanse mode. Thus, in some embodiments, for either and/or both denuding and cleansing of the bone, a speed of below about 5000 rpm may be appropriate, typically between about 10 rpm to about 5000 rpm, and more typically between about 10-1000 rpm. If the tool shaft or barrel is rotated during cauterizing, the speed may be different for the cauterizing, the denuding and the tissue cleansing/scraping. In some embodiments, the speed for each is between about 10 to about 5000, including about 125 rpm, about 150 rpm, about 200 rpm, about 250 rpm, about 300 rpm, about 350 rpm, about 400 rpm, about 450 rpm, about 500 rpm, about 550 rpm, about 600 rpm, about 650 rpm, about 700 rpm, about 750 rpm, about 800 rpm, about 850 rpm, about 900 rpm, about 950 rpm, about 1000 rpm, about 1500 rpm, about 2000 rpm, about 2500 rpm, about 3000 rpm, about 3500 rpm, about 4000 rpm, about 4500 rpm and about 5000 rpm.

In some embodiments, the speed is low speed for one or both the denuding (with or without cauterizing) and the cleansing. The term "low speed" means between about 10 rpm to about 100 rpm, including about 10 rpm, about 15 rpm, about 20 rpm, about 30 rpm, about 40 rpm, about 45 rpm, about 50 rpm, about 60 rpm, about 70 rpm, about 80 rpm, about 90 rpm and about 100 rpm.

While not necessary, the tool 10 can have a cleanse run mode that rotates the therapy delivery tool head 15 at a slower speed than a denuding speed. In some embodiments, the tool 10 can have a substantially constant rpm with a controlled maximum output of maximum operational capacity at full speed of between about 10 rpm to about 5000 rpm, typically between about 10 and 200 rpm, and more typically with a maximum rotational speed of between about 10 rpm to about 100 rpm.

As discussed above with respect to FIG. 8A, the tool 10 can include a circuit C that has a speed limiter control 77 to insure that the maximal rotational speed allowed is between about 10-5000 rpm. The use of properly sized gears/clutches, speed governors, electronic cut off sensors or other mechanisms can be used to control the maximal speed.

The tool 10 can be configured to have a maximum speed (at full speed) that is between about 10 to about 5000 rpm, typically between about 10-1000 rpm such as between about 10-500 rpm or between about 10-100 rpm including about 40 rpm, about 45 rpm, about 50 rpm, about 55 rpm, about 60 rpm, about 65 rpm, about 70 rpm, about 75 rpm, about 80 rpm, about 85 rpm, about 90 rpm, about 95 rpm and about 100 rpm.

In some embodiments, a viewing scope can be placed in the cannula 30 or in an adjacent cannula or port (not shown) to allow real time viewing of the spinal joint J during the therapy.

The denuded soft capsular tissue can be suctioned via vacuum or otherwise removed by the spinal facet therapy (e.g., debrider) tool 10 and/or via the guide cannula 30 and vacuum port 40v or with another tool. In some embodiments, the tool barrel 10b can be in fluid communication with an irrigation source and/or a vacuum/suction source. The tool barrel 10b can comprise an irrigation channel and a suction/vacuum channel with respective ports on the distal end of the tool 10d (see, FIGS. 25C and 26 of the co-pending application incorporated by reference hereinabove). A single channel can be used for both irrigation and suction where both functions are provided. In some embodiments, no tissue removal is required.

The surgical site J can be flushed out with saline or other suitable cleansing liquid and suctioned and removed. The flushing of the site can be carried out using the tool 10 or without the tool 10. If the latter, the tool barrel 10b can reside in the cannula 30 during the irrigation and/or suction. The cannula 30 may remain in place during the flushing or removed before this action. The tubular support member 40, where used, can be removed before or after the guide cannula 30. The therapy delivery tool 10 can be removed before, after or with removing the cannula 30. The guide pin 20 can be removed before, after or with the tool 10 and/or cannula 30 (or even earlier if not needed according to some embodiments, for example).

This procedure can be repeated for each joint selected for treatment. Typically, between two and six joints J can be treated at one therapy session.

In some embodiments, to save time, all of the guide pins 20 on one side for each joint J can be placed before any incisions and/or before debriding at any level. Sterile surgical tape such as 3M™ Steri-Strips™ and/or a small suture (or surgical glue) can be placed to close a respective incision wound once the therapy is complete.

Post-pin placement, the entire spinal facet treatment procedure for one joint J can take between five to fifteen minutes. The procedure can be an outpatient procedure and the patient can typically walk the same day with recovery over a week to let the surgical sites heal.

FIG. 12 illustrates an example of a spinal facet debridement surgical tool kit 75. As shown, the kit 75 can include a package 75p with sterile components that facilitate the surgery. The kit 75 can include a debrider tool 10 (which can be the entire therapy delivery tool 10 or a consumable, single use disposable or multi-use barrel 10b), optionally a plurality of guide pins $20_1$, $20_2$ (shown as two, but one or more than two can be provided, or the pins can be provided separately outside the kit), a dilation tube 50 and at least one guide cannula 30 (or working tube), and the tubular support 40. The kit 75 may also include the hand grip member 200. While shown as kits with all the noted components for facilitating ease of surgical preparation, the components may be provided as separate units or sub-sets.

The guide cannula 30 can be provided pre-attached to the dilation tube 50 or hand grip 200, or may be provided as a separate unassembled component. For bilateral and/or multilevel procedures, more than one guide cannula 30 and, where used, more than one tubular support 40, may be included, and if so, may be labeled for right and left sides and/or for indicating spinal treatment levels. The guide pins 20 can be provided in a common size or different sizes, typically with a diameter that is between about 0.75-1.25 mm, more typically about 1.0 mm.

Figure 13:
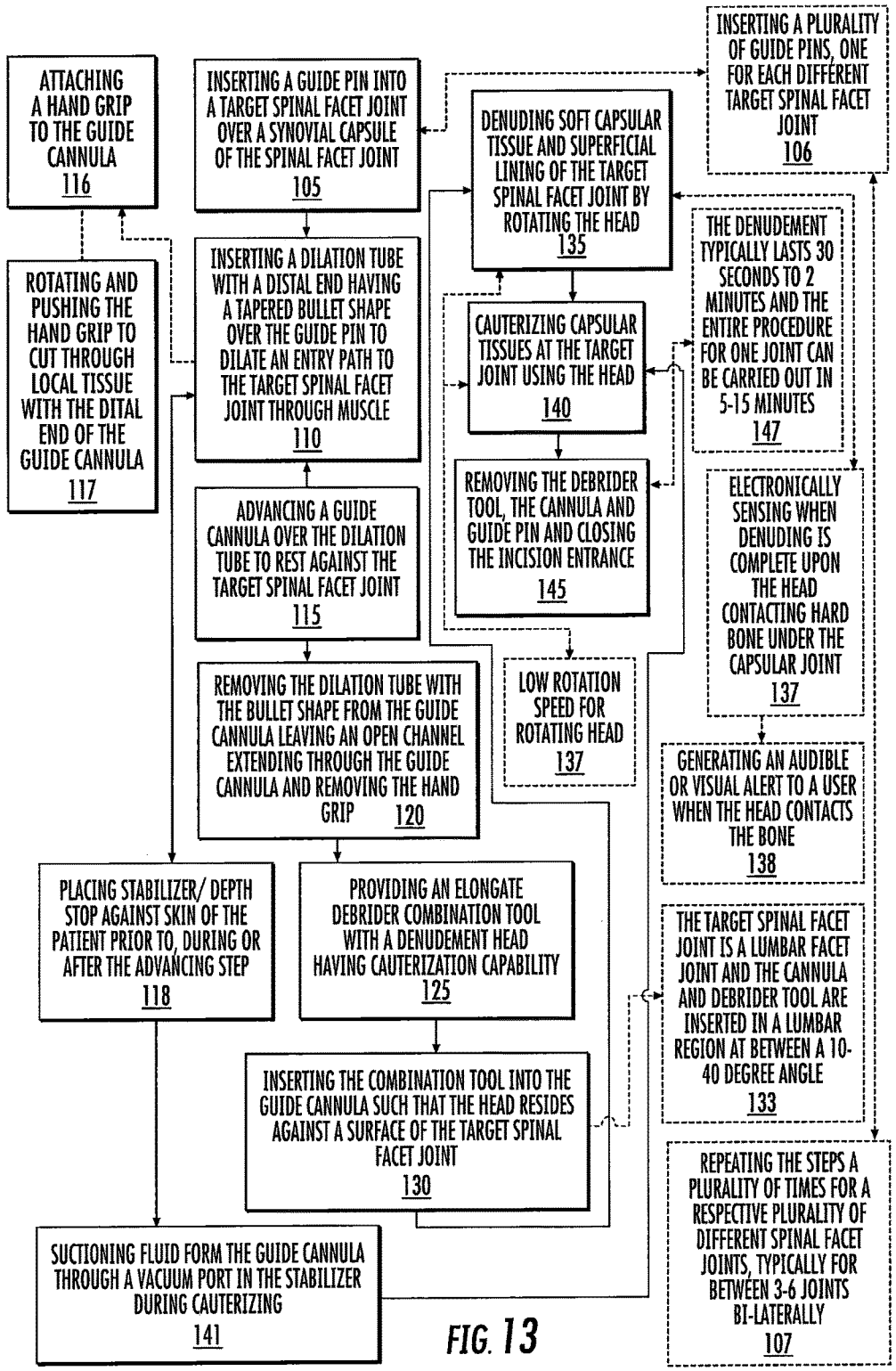
FIG. 13 is an exemplary flow chart of steps that can be used to carry out surgical procedures according to embodiments of the present invention.

FIG. 13 is a flow chart of exemplary actions that can be used to carry out a spinal facet treatment to alleviate pain associated with arthritis. A guidewire/pin is typically inserted into a target spinal facet joint over a synovial capsule of a spinal facet joint (block 105). A dilation tube with a distal end having a tapered bullet shape is inserted over the guide pin to dilate an entry path to the target spinal facet joint through muscle (block 110). A cannula is slidably advanced over the dilation tube to rest against the target spinal facet joint (block 115).

A hand grip can be attached to the guide cannula (block 116) before, during or after the advancing step. A user can concurrently rotate and push the hand grip to thereby rotate and push the distal end of the guide cannula to cut through local tissue and position the distal end of the guide cannula at the target intrabody site (block 117). The dilation tube with the bullet shape can be removed, as can the hand grip and optionally the k-wire/pin (in no particular order), leaving the guide cannula with an open channel extending therethrough in position (block 120). An external tubular support (optionally with an external stabilizer having an enlarged base) can be placed against the skin of the patient prior to, during or after the guide cannula is advanced (block 118). A user can press down against the tubular support member 40 (typically against the base 40b) to hold the tubular support member in a desired alignment orientation and position relative to the target spinal facet joint prior to removing the dilation tube and/or inserting the guide cannula. In some particular embodiments, the tubular support is placed on the patient after the hand grip and/or dilation tube are removed.

An elongate debridement tool with a denudement head having cauterization capability ("combination tool") is provided (block 125). The combination tool is inserted into the cannula such that the head resides against a surface of a target spinal facet joint (block 130). Soft capsular tissue and a superficial lining of the target spinal facet joint are denuded by rotating the head (block 135). Tissue at the target joint is cauterized using the head (block 140). Fluid (i.e., hot air) is suctioned from the guide cannula using a vacuum port in the tubular support out of the patient during the cauterizing (block 141) to thereby reduce heat in the guide cannula.

The treated joint can be flushed and suctioned. The therapy delivery (e.g., debrider) tool, cannula and guide pin can be removed and the incision entrance closed (block 145).

In some embodiments, the denuding and/or cauterizing can be carried out using a low rotation speed for the rotatable tool head (block 137).

In some embodiments, a plurality of guide pins can be inserted, one for each different target spinal facet joints (block 106). Steps 110, 115, 120, 130, 135, 140 and 145 can be repeated at each respective different spinal facet joint, typically between 2-6 joints, including 2 joints, 3 joints, 4 joints, 5 joints and 6 joints (block 107). Usually two or three levels, bilaterally, are debrided during a single surgical session.

The denudement typically lasts between about 10 seconds to 3 minutes (average), more typically between about 20 seconds to 40 seconds (average), and the entire procedure (post pin placement or including pin placement) for one joint can be carried out in about 5-15 minutes (typically bilaterally per joint) (block 147).

The head 10 can be configured to denude and cauterize soft tissue at the target spinal facet joint either serially (e.g., intermittently or interleaved) and/or concurrently. The tool 10 can allow a user to select when to cauterize or it can be configured to automatically cauterize during the entire denuding action, during a portion of the denuding action, or after a denuding action.

In some embodiments, the method can include electronically sensing when denuding is complete upon contact with bone under the capsular joint (block 137). The method may optionally include electronically generating an audible or visual alert to a user when the head contacts the bone and/or when the denuding of soft tissue is complete (block 138).

In some embodiments, the target spinal facet joint is a lumbar facet joint and the cannula 30 and debridement tool 10 can be inserted in a lumbar region at between a 10 to about a 40 degree angle, typically between about 20-30 degrees for this region (block 133). Other levels, e.g., cervical and thoracic debridement may be at other angles typically between about 0 to about 10 degrees.

It will be appreciated that angulation of the tool 10 can change depending on scoliosis, etc. Typically, the lumbar region is between about 10 to about 40 degrees as noted above. However, the angulation is appropriate so as to be perpendicular to the target spinal facet joint surface, which is usually about 10 to about 40 degrees laterally in the lumbar region and between about 0 to about 10 degrees laterally in the thoracic and cervical regions.

In some embodiments, the order of use of the components where the tubular support 40 is used can be: insert the guide pin 20, then insert the dilator tube 50. Next, the tubular support 40 can be placed on the skin S over the guide pin 20 and/or dilator tube 50. The dilator tube 50 can then be removed if it was used. The guide cannula 30 and/or therapy tool 10 can be inserted through the tubular support member 40 with or without the guide pin 20 in place (that is the guide pin 20 can have been previously removed or removed after the cannula 30 and/or tool 10 are inserted through the member 40). The tool 10 can deliver the therapy to the facet joint J with the pin in position and extending through the pin bore 11 or the therapy to the facet joint can be applied after the pin 20 is withdrawn.

Figure 14A:
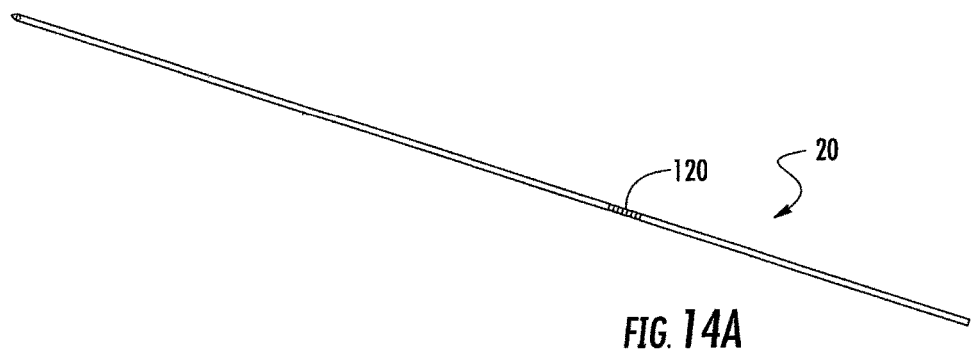
FIGS. 14A-14G illustrate cooperating components that facilitate a spinal surgery according to embodiments of the present invention.
Figure 14B:
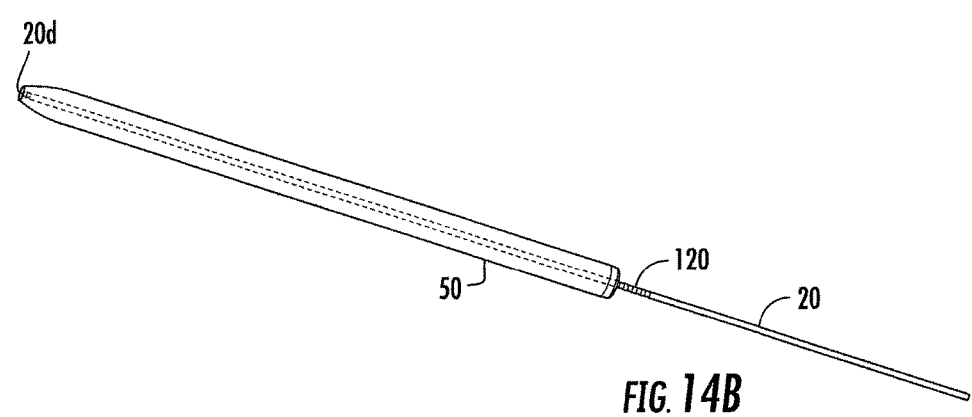
Figure 14C:
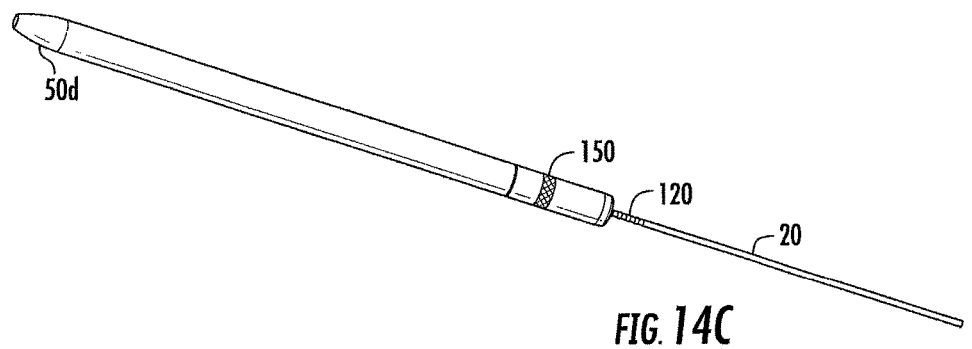
Figure 14D:
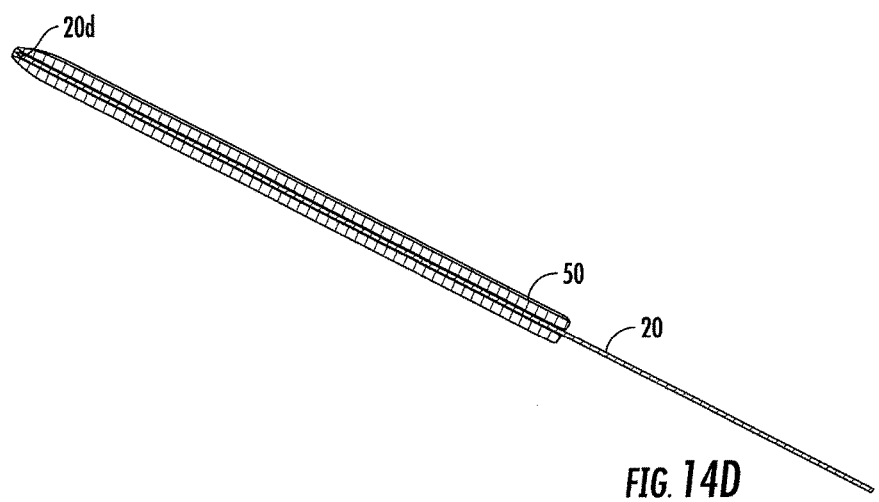
Figure 14E:
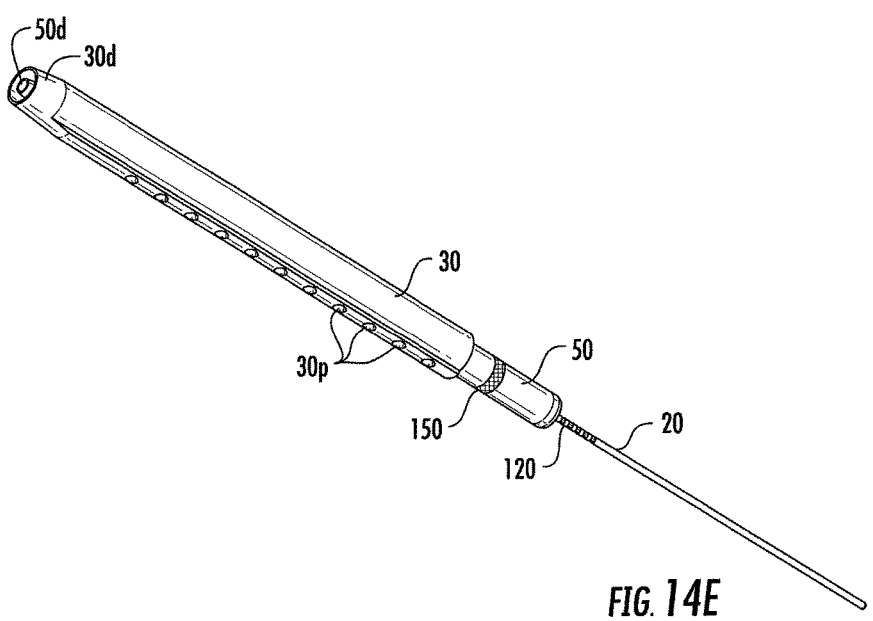
Figure 14F:
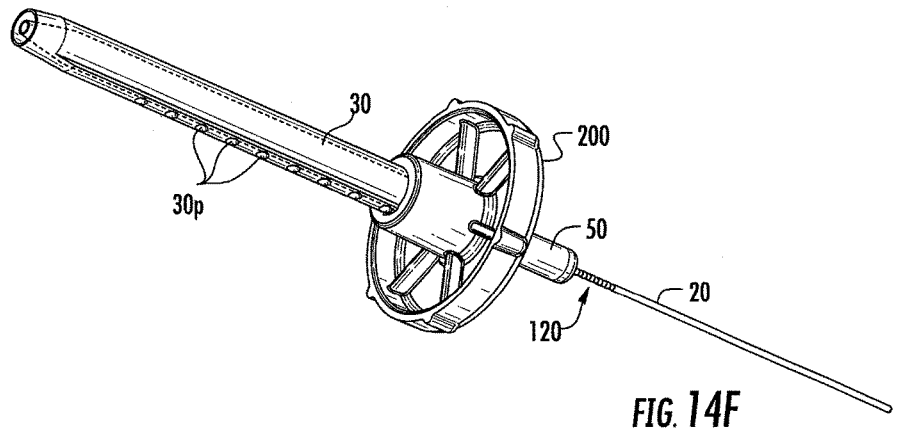
Figure 14G:
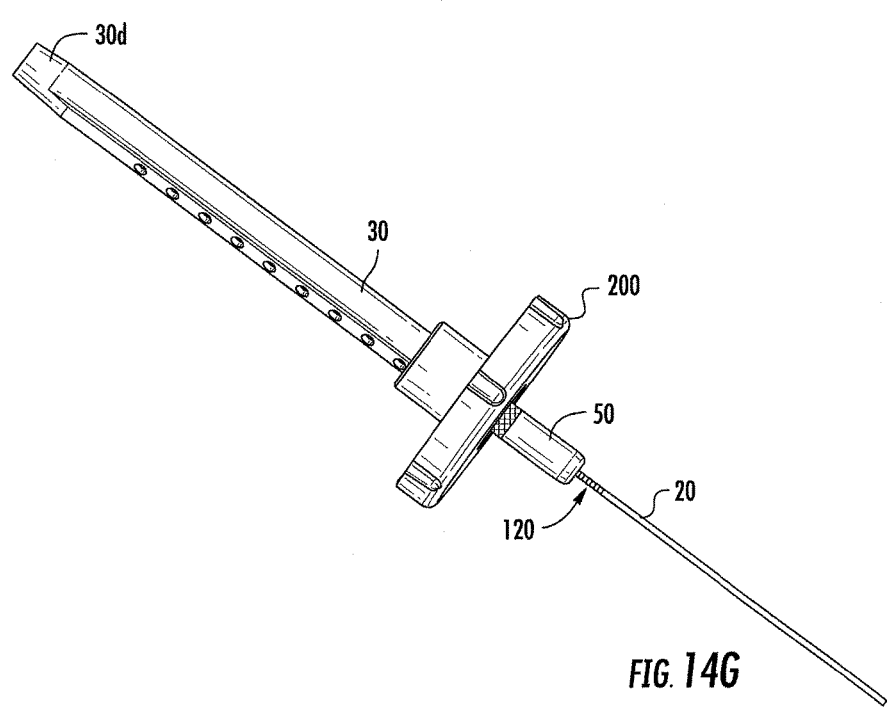

In some embodiments, the order of use of the surgical tools can be as shown, in serial order with respect to the next set of noted figures: insert guide pin or k-wire 20 (FIG. 14A), insert dilator 50 over the pin/wire 20 (FIG. 14B), insert guide cannula 30 over dilator 50 (FIG. 14E), then attach the hand grip 200 (FIG. 14F). As discussed above, the hand grip 200 can be (typically manually) rotated and pushed concurrently to cut through adjacent tissue and place the distal end of the guide cannula 30d at the target spinal facet treatment site J. Where a detachable hand grip 200 is used, the hand grip 200 can be removed from the guide cannula 30 before the tubular support 40 is attached. FIGS. 14C, 14E and 14G illustrate that the dilator 50 may also include visual indicia 150 to allow a user to align/ascertain a depth thereof relative to the guide pin visual indicia 120, for example. The guide pin/k-wire 20 can have a sharp distal end 20d (FIGS. 14B, 14D). FIGS. 14B and 14F illustrate that the dilator 50 may be visually transmissive.

The stop depth provided by the tubular support 40 and/or tubular support and guide cannula 30 combination may be adjustable. The clinician can decide an appropriate stop depth for the patient prior to placing one or more of the components in the patient.

The base 40b of the tubular support or held by the tubular support 40 can also be placed on the skin S before or after the guide pin 20 is inserted at the treatment joint J. The tubular support 40 may have or hold a stabilizer with a bottom surface 40b that can releasably attach to skin of the patient via adhesive or vacuum and the like and define an entry portal for the procedure.

The entire tool 10 with the cable 13 can be sterile and single use disposable.

The tool 10 can be configured to inhibit re-use. For example, the tool 10 can have a reuse restriction circuit 180 as shown in FIGS. 8A-8C. The reuse restriction circuit 180 can be in communication with the processor P or configured as part of the processor P itself or partly held on the processor P, the circuit C and/or partly in a separate circuit of the tool 10. The reuse restriction circuit 180 can include or be in communication with one or more of a time-out circuit 180t, an on and/or off counter 180c (to control a defined number of power-up, power down operations and/or a number of successive power up and power downs, for example), and/or a self-destruct circuit 180d, to automatically disable the device 10 from being able to operate to thereby restrict further use. The self-destruct circuit 180d can be configured to destroy certain components and/or functionality of the tool 10. The time-out circuit 180t can be configured to shut down or not power up after a power off and/or after a defined time from a defined trigger event. The on/off counter 180c can be configured to limit the number of on/off uses to less than 10, typically between 3-6, to allow for multiple level treatments and allow a user to power-off between levels.

The "trigger" event, can be based on one or a combination of a power-on or power off-event of the tool 10, electronic detection of a cautery output at the end of the barrel of the tool, which may be determined using a temperature or other sensor on the end of the tool 10. The trigger event can be an active denuding time or an active cleansing time, post cauterization, associated with motor rotation. The trigger event can be based on a logic control of the processor P based on a plurality of pre-defined trigger event conditions to start the time period such as (a) the tool being in a power-on state, (b) the presence of a cautery temperature at the tool barrel, and (c) rotation of the motor. The defined time may be sufficient to allow for multiple spinal facet levels to be treated for a respective patient using one tool 10, thus the time, when electronically sensed can be a cumulative time based on active motor time, time from power on, a defined number of power on/power off events, and the like. The defined time can be less than about 1 hour, typically between about 5 minutes to about 30 minutes, such as about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 25 minutes and about 30 minutes, for example.

As shown in FIG. 8B, by way of example only, the tool circuit C can include a reuse restriction circuit 180 that includes a self destruct circuit 180d that can carry out a self destruct mode based on one or more defined parameters. In some embodiments, the one or more defined parameters includes a pre-defined time period, which may be automatically timed using a clock or timer in communication with the reuse restriction circuit 180, typically in the processor P of the circuit 10. The clock or timer can be configured to time a period of allowable operation based on a power on a "trigger" event as described above and may be any of the time periods described above and/or trigger based on defined trigger event conditions as discussed above.

As shown in FIG. 8B, the tool can generate an audio and/or visual output 180a to alert a user that the tool 10 has been self-destructed to destroy functionality of the tool 10. The output 180 may be a flashing (e.g., red) LED or other alert indicator. As shown by the circles with the X, the self-destruct mode can be configured to disable or destroy operational capability of the processor P and/or disconnect or destroy an electrical connection 10c from one or more internal component such as the battery B or the cautery input 80i. The self-destruct mode can use the battery B or the cautery generator 80 via input 80i to electrically destroy one or more internal components or electrically or mechanically disconnect power such as by cutting a wire or cord in a power cable or connector associated with same, for example after a time out period and/or an attempt to power-on after the first authorized use, e.g., after 30 minutes from an initial power up.

In some embodiments, the self destruction circuit 180d can be configured so that if the surgical tool 10 is disconnected (after a first operation or "on" potentially for a defined time) from a physical connection, e.g., plug in, to the generator 80 or generator unit 80h (FIG. 8C), the device 10 will self-destruct. In some embodiments, circuitry C in communication with (typically onboard) the device 10 can be configured to sense that a power connection has been terminated and automatically destroy functionality of one or more components. The tool 10 cannot function to operably connect to a generator 80 or generator housing 80h for a second power on, (e.g., a second surgical case).

FIGS. 7A, 7B and 7C also illustrate that the shaft 18 extends to the rotating head 15 and can be configured with a fluted configuration 15f to inhibit tissue clogging during denuding or tissue scraping. The fluted configuration can have curvilinear longitudinally extending recesses 15r.

The flutes 15f can be straight or curvilinear. The flutes 15f can be thin, e.g., between about 1 mm to about 5 mm. The flutes 15f can extend longitudinally over a small portion of the length of the shaft and/or barrel 10b, such as between about 3 mm to 1 inch, or over substantially a length of the shaft and/or barrel 10b sufficient to extend through the working cannula 30, e.g., a length between about 50 mm to about 200 mm, including about 50 mm, about 75 mm, about 100 mm, about 150 mm and about 200 mm. The head lateral dimension can be between about 3-15 mm (if a non-expandable configuration is used) and between about 3-25 mm if an expandable version is used. In some embodiments, a maximal distal head lateral dimension with the flutes 15f can be between about 5-15 mm such as about 5 mm, about 6 mm, about 7 mm, about 8 mm, about 9 mm, about 10 mm, about 11 mm, about 12 mm, about 13 mm, about 14 mm, and about 15 mm.

As shown in FIGS. 7A, 7B and 7C, the head 15 can include a single medially-located linear conductive electrocautery segment 15e. The linear cautery element 15e can be continuous and extend across the entire face of the head 15. As shown in FIG. 7B, the linear cautery element 15e bisects the face of the tool head 15 and can separate two opposing, non-conductive scraping members 15s. The scraping members 15s can comprise PEAK or PEEK material, for example. The scraping members 15s may extend a distance of between about 0.5 mm to about 5 mm beyond the cautery element 15e. The scraping members 15s can be used for both denuding, before cauterization and tissue cleansing (post cauterization), but typically a concurrent cautery and scraping action is carried out, by rotating the head at a low rpm during cautery, typically between 10 and 100 rpm, as discussed above.

The head 15 can be a monolithic unitary member with the electrocauthery surface(s) 15e and flutes 15f. FIG. 7C illustrates that the shaft can further include longitudinally spaced apart notches 15n. The entire shaft with the head can be a monolithic conductive member. The head 15 and/or shaft with the head can be a suitable medical grade electrically conductive material such as stainless steel. The head 15 may comprise a discrete electrocautery member 15e that is of a different material than the fluted shaft 15f. That is, as shown, the discrete electrocautery member 15e can reside in or extend from a non-conductive (electrically insulating) shaft 18 and/or barrel 10b. The discrete electrocautery member 15e can be configured to slidably, longitudinally extend and retract relative to the adjacent non-conductive shaft or barrel or may be statically affixed to same.

FIGS. 15A-15C, 17A, 17B, 18A and 18B illustrate other embodiments of the surgical tool set comprising the hand grip 200, the guide cannula 30 and the tubular member 40'. In these embodiments, the tubular member 40' can define an internalfluid chamber 47 that extends above the base 40b and below the top 40u of the tubular member 40t can allow vacuum and/or heated air to be flowably directed about the exterior of the guide cannula 30, typically allowing 360 degrees of open interior to allow vacuum to flow about the guide cannula 30, inside the closed space of the fluid chamber 47, under the vacuum arm 40v.

The fluid chamber 47 can have an upper portion 48 and a lower portion 49, each that abuts the outer surface of the guide cannula 30 to close the chamber 47. The chamber 47 may comprise a sealant and/or provide upper and lower end portions 48, 49 with a sufficiently tight attachment to provide a suitable air flow path to the vacuum portal 40v. Hot fluid (i.e., gas or air) can be directed to exit the portal tube 30 via the vacuum tube 40v and/or the guide cannula 30 above the vacuum tube 40v (as indicated by the arrows representing flow in FIGS. 15B, 18B). The fluid chamber 47 can have an inner wall 47w that transitions outward from the upper and lower ends 48, 49 to provide a greater volumetric region between the upper and lower ends 48, 49, thereof. The vacuum portal 40v can reside above the upper end 48 of the fluid chamber 47. A fluid path 48p can extend between the upper end of the chamber 48 and the vacuum portal/arm 40v. The upper and lower ends 48, 49 of the fluid chamber 47 may include inwardly extending ledges that reside adjacent an outerwall of the guide cannula 30. These configurations do not require alignment of the guide cannula 30 in the tubular support 40' and the guide cannula 30 can be "keyless".

Figure 15A:
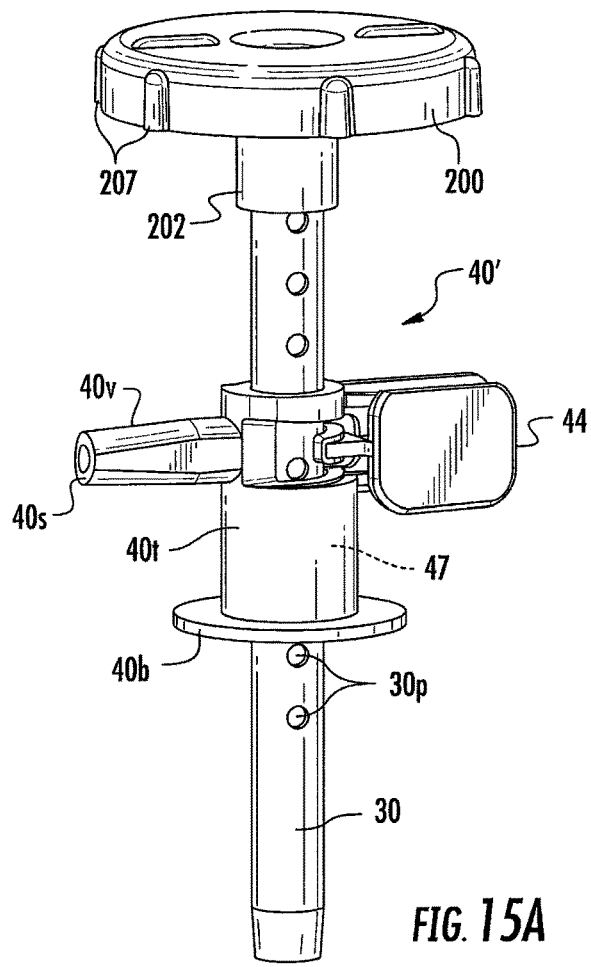
FIG. 15A is a side perspective view of a surgical tool set for a surgical procedure according to embodiments of the present invention.
Figure 15B:
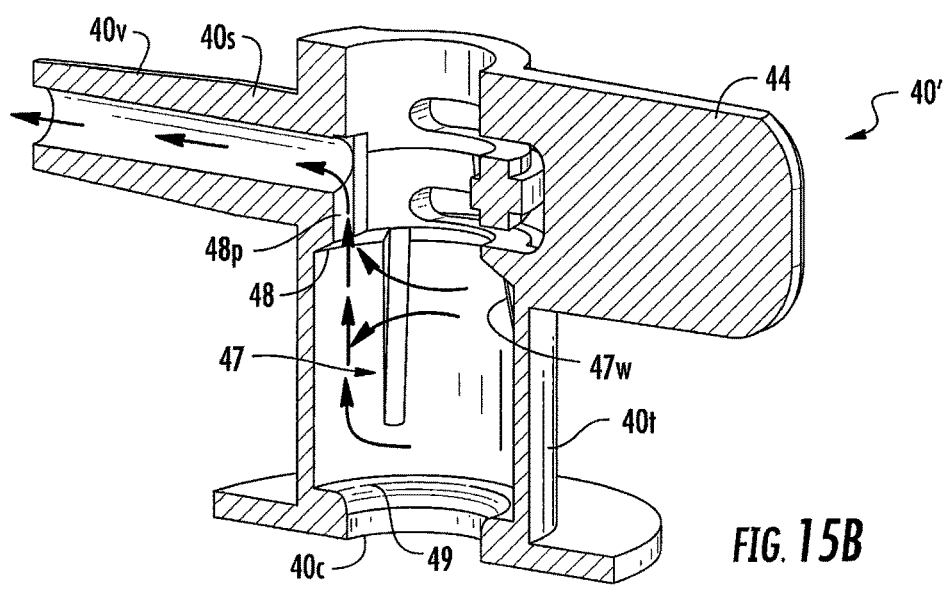
FIG. 15B is a greatly enlarged section view of the tubular support member shown in FIG. 15A according to embodiments of the present invention.
Figure 15C:
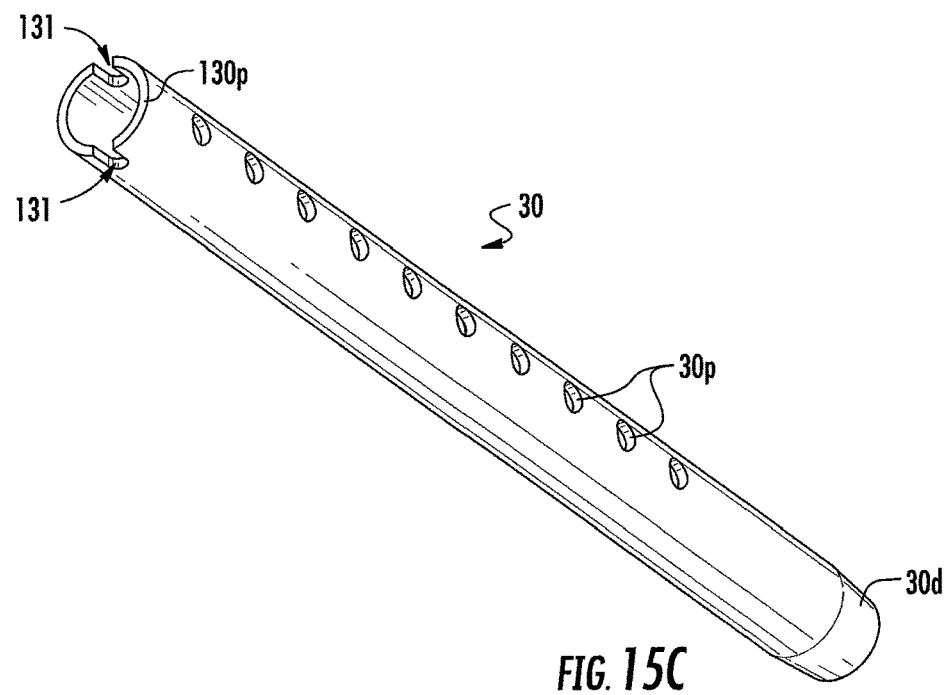
FIG. 15C is an enlarged, side perspective view of the guide cannula shown in FIG. 15C according to embodiments of the present invention.
Figure 16:
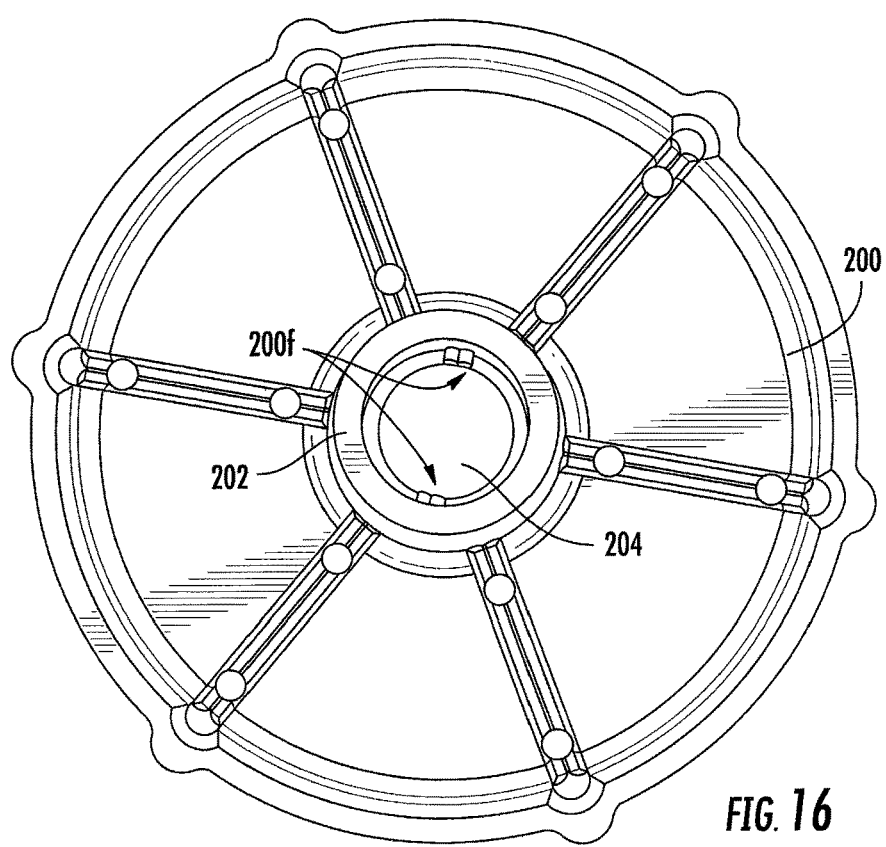
FIG. 16 is a greatly enlarged top, perspective view of a portal driver according to embodiments of the present invention.

As shown in FIG. 15C, for example, the word "keyless" means that the guide cannula 30 does not require a longitudinally extending recess or protrusion holding the ports 30p so that it can reside in (typically attach to) the tubular support 40' and operate at any orientation in the fluid chamber 47 with its ports 30p at any orientation therein relative to the tubular support/vacuum portal 40v. FIG. 15C also illustrates that the proximal end 130p of the guide cannula 30 can include at least one downwardly extending slot or notch 131, shown as circumferentially spaced apart (diametrically opposing) notches 131 that can engage downwardly extending flanges (i.e., protrusions) 200fn the handle grip member 200 about the wall of the interior channel 204 as shown in FIG. 16.

The guide cannula 30 can have a length (typically the entire length) of at least the lower portion with a maximal outer diameter that is between 7 mm and 15 mm, typically about 10 mm.

Figure 17A:
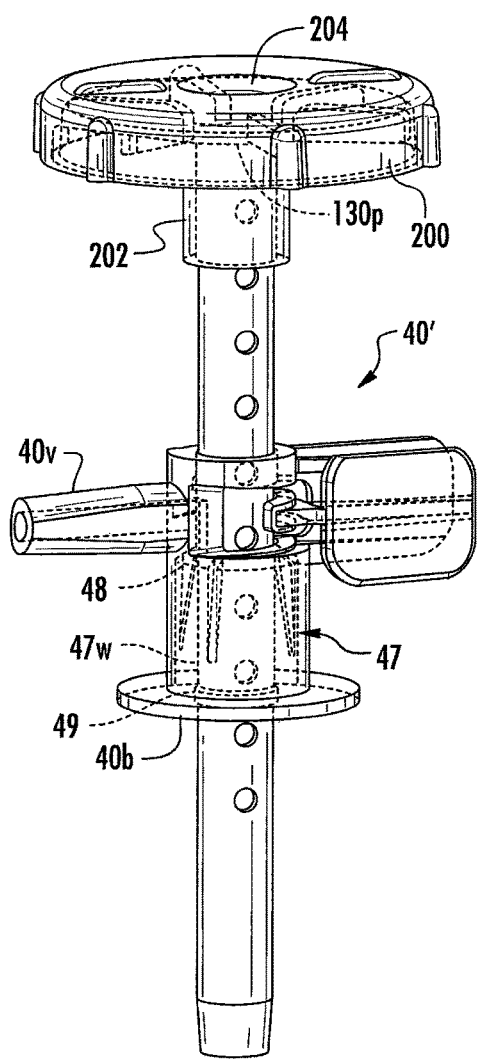
FIG. 17A is a partially transparent view of the surgical tool set shown in FIG. 15A illustrating certain internal features according to embodiments of the present invention.
Figure 17B:
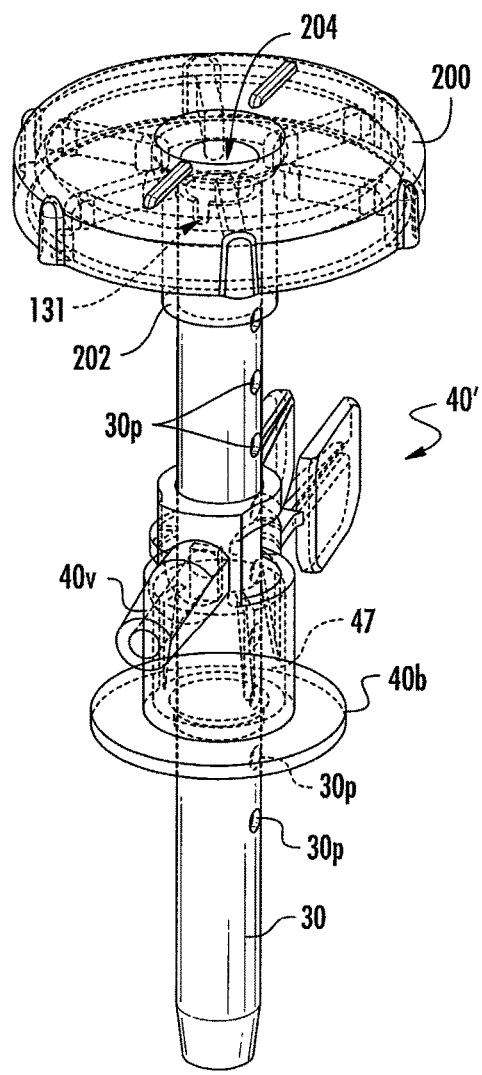
FIG. 17B is a partially transparent view of the surgical tool set shown in FIG. 15A illustrating certain internal features according to embodiments of the present invention.

FIGS. 17A and 17B illustrate the embodiment shown in FIG. 15A with the tubular member 40' shown such that the fluid chamber 47 extends a longitudinal length sufficient to hold a plurality of longitudinally extending ports 30p between the upper and lower ends 48, 49, shown as two, but the chamber 47 and/or ports 30p may be configured so that the chamber 47 holds only one or more than two ports 30p.

Figure 18A:
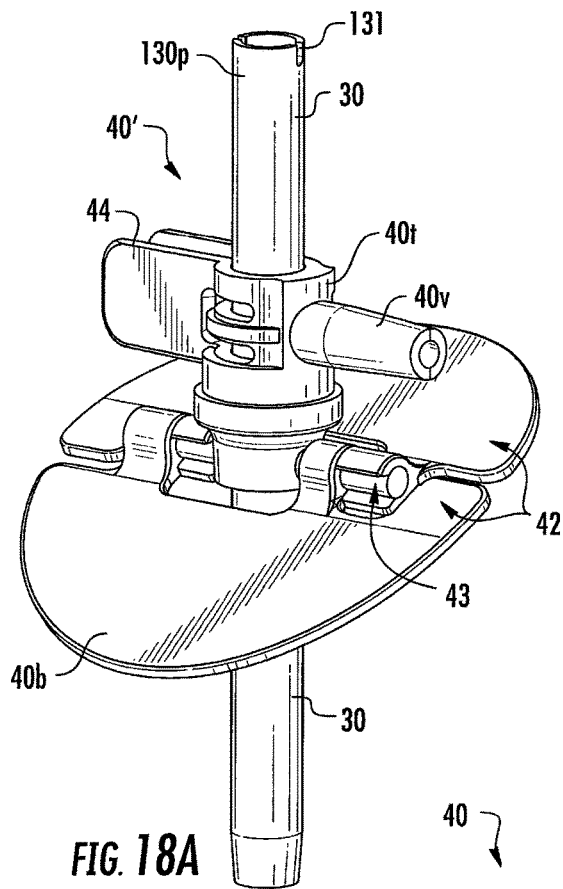
FIG. 18A is a side perspective view of a surgical tool set for a surgical procedure according to embodiments of the present invention.
Figure 18B:
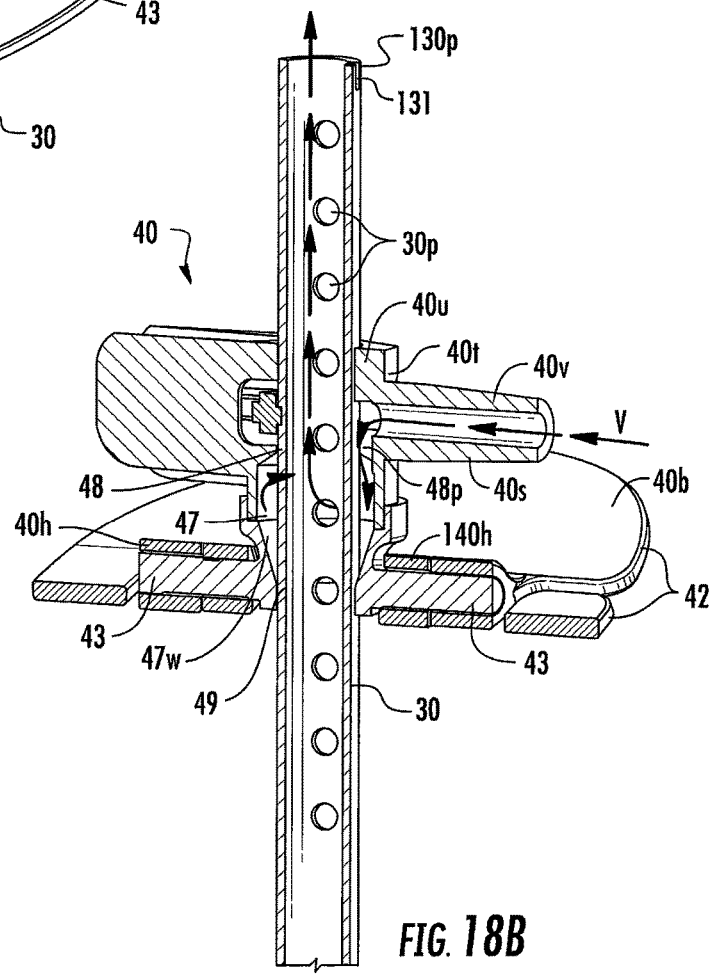
FIG. 18B is a section view of the tool set shown in FIG. 18A according to embodiments of the present invention.

FIGS. 18A and 18B illustrate the tubular member 40 with the fluid chamber 47 hinged and with a base 40b. The base 40b can have first and second wings 42 that are hingeably connected to the tubular member 40t via outwardly extending arms 43. The arms 43 can reside under the vacuum portal 40v and comprise a glass filed material for suitable frictional engagement/movement of the arms 43 to allow a pivoting action of the wings 42 to accommodate different positions and patients. Again, the guide cannula 30 can have a keyless configuration and may include the downwardly extending notches on an upper end thereof 130p to engage the portal driver 200. Additional discussion of hinged base configurations are described in, co-assigned U.S. patent application Ser. No. 62/091,226, and PCT/US2015/064988, the contents of which are hereby incorporated by reference as if recited in full herein.

Figure 19A:
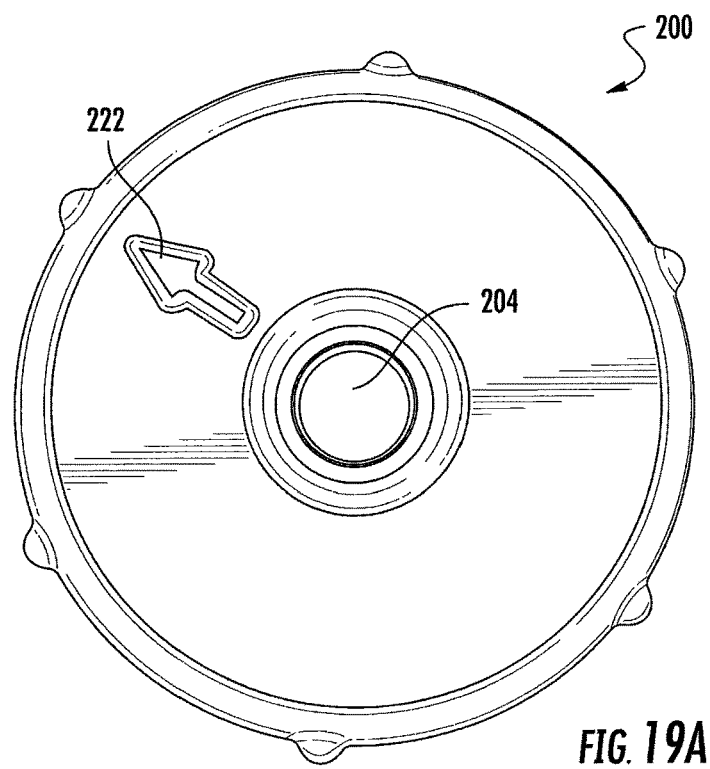
FIG. 19A is a greatly enlarged top view of a portal driver according to embodiments of the present invention.

FIG. 19A illustrates that the portal driver 200 can include visual indicia 222 on an upper surface thereof. The visual indicia 222 can provide a user with a visual prompt for positional alignment with the guide cannula 30. The visual indicia 222 can be an arrow that faces the outer perimeter of the hand grip 200.

Figure 19B:
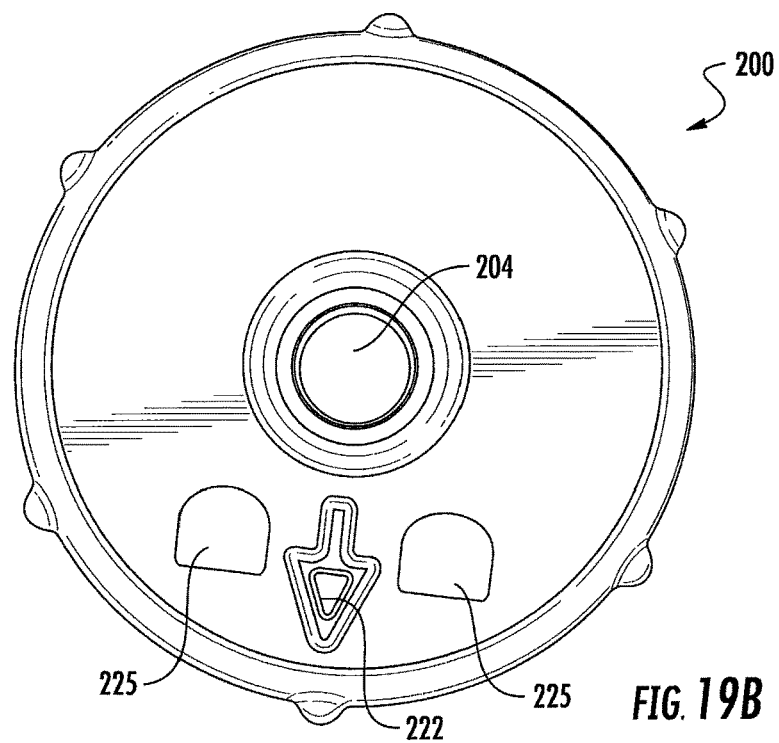
FIG. 19B is a greatly enlarged top view of another embodiment of a portal driver according to embodiments of the present invention.

FIG. 19B illustrates that the portal driver 200 can include at least one window 225 that provides a visually open region between the outer perimeter of the upper end of the handle and the tube to allow a clinician to be able to see what components are under the portal driver 200 during use and/or during assembly. The at least one window 225 may be a single window of any shape. As shown, the at least one window 225 resides adjacent the visual indicia 222, shown as a window 225 on each side of the visual indicia 222. The window 225 can be an open aperture or may comprise a visually transmissive (typically transparent) material. It is contemplated that the spinal facet debridement procedure with the combination debrider tool 10 can allow the spinal debridement procedure to be carried out by general surgeons, radiologist, pain medicine, physical medicine, orthopedic and neurosurgeons and/or allow more surgeons to be able to competently carry out the procedure thereby providing more global access to this treatment for patients with longer term pain relief and obviating the need for follow-up treatments upon nerve renervation at the treated spinal facet joint(s).

Embodiments of the invention provide treatment methods that can be carried out at an outpatient clinic and/or as an outpatient procedure at a hospital or surgery center.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. A spinal facet therapy system, comprising:
a spinal facet therapy tool with an elongate rotatable shaft, the shaft having a distal end with a cautery element, the tool in communication with the electrosurgical generator, wherein the tool is configured to automatically rotate at between about 10 rpm to about 5000 rpm and is adapted to remove an end plate receptor region comprising a synovial capsule of the spinal facet joint, and wherein the electrosurgical generator supplies power to the cautery element while the shaft rotates or is stationary;
a guide cannula with at least one fluid port extending through a longitudinally extending wall thereof, the guide cannula configured to hold the tool shaft during an active treatment;
an external tubular support member residing against skin of a patient and holding the guide cannula therein during the active treatment, wherein the external tubular member comprises at least one vacuum port in fluid communication with the guide cannula at least one fluid port and a vacuum source to thereby suction heat from the guide cannula when the cautery element is cauterizing; and
a hand grip member configured to detachably couple to the guide cannula to thereby allow a user to concurrently rotate and push against the guide cannula to place the guide cannula in a desired position prior to inserting the tool shaft into the guide cannula.

2. The spinal therapy system of claim 1, wherein the hand grip member has an open center channel extending therethrough that releasably engages a proximal end of the guide cannula.

3. The spinal therapy system of claim 1, further comprising a k-wire or guide pin that has visual markings thereon for allowing a user to determine a depth of a distal end of the guide cannula relative to the k-wire or guide pin when the k-wire or guide pin is in bone at a target spinal facet joint.

4. The spinal therapy system of claim 1, wherein the hand grip member comprises visual indicia of orientation on an upper surface thereof and/or at least one window extending between an outer perimeter of the upper surface and the open center channel.

5. The spinal therapy system of claim 1, wherein the external tubular support member comprises an upwardly extending tube with an upwardly extending through channel defining a fluid chamber, wherein the fluid chamber has an inner wall with upper and lower ends, wherein the inner wall travels laterally outward a distance as it moves longitudinally away from each of the upper and lower ends to define an increased volumetric segment extending about the perimeter of the outerwall of the guide cannula, wherein the upwardly extending tube includes a vacuum port extending therethrough residing above the upper end of the fluid chamber and in fluid communication with the fluid chamber, wherein the upwardly extending tube holds an arm that extends away from an axial direction of the tube about the vacuum port, and wherein the arm is adapted to attach to a conduit to engage a vacuum source.

6. The spinal therapy system of claim 1, wherein the guide cannula has a keyless outer surface that holds a plurality of longitudinally spaced apart ports.

* * * * *